(12) United States Patent
Fidacaro et al.

(10) Patent No.: US 8,233,272 B2
(45) Date of Patent: Jul. 31, 2012

(54) DISPLAY UNITS FOR USE IN MONITORING PATIENTS AND RELATED SYSTEMS AND METHODS

(75) Inventors: James Fidacaro, Mountain Lakes, NJ (US); James Patrick Thrower, Oakland, NJ (US); Geoffrey C. Jawidzik, Mahwah, NJ (US); Nicholas Barker, Laguna Beach, CA (US); Allan Cameron, Natick, MA (US); Brian Stonecipher, Ashland, MA (US); Jim Wilson, Norwood, MA (US); David Chastain, Boston, MA (US)

(73) Assignee: Mindray DS USA, Inc., Mahwah, NJ (US)

( * ) Notice: Subject to any disclaimer, the term of this patent is extended or adjusted under 35 U.S.C. 154(b) by 213 days.

(21) Appl. No.: 12/862,498

(22) Filed: Aug. 24, 2010

(65) Prior Publication Data

US 2011/0054268 A1  Mar. 3, 2011

Related U.S. Application Data

(60) Provisional application No. 61/236,798, filed on Aug. 25, 2009.

(51) Int. Cl.
  *G06F 1/16* (2006.01)

(52) U.S. Cl. .................. 361/679.04; 710/304; 600/484; 340/870; 362/157

(58) Field of Classification Search .............. 710/8, 303, 710/304; 361/679.22, 679.44, 679.41, 679.43, 361/679.08, 679.58, 679.33, 679.02, 679.4, 361/679.57, 679.17, 679.55, 679.27, 679.06, 361/679.21, 679.29; 600/300, 301, 484, 600/566, 431, 323; 340/539.12, 870, 573.1, 340/685, 870.02; 362/206, 235, 157; 455/557, 455/415, 420, 556.1, 566
See application file for complete search history.

(56) References Cited

U.S. PATENT DOCUMENTS

| | | | |
|---|---|---|---|
| 7,499,272 B2 * | 3/2009 | Searby et al. ............ | 361/679.22 |
| 2011/0047298 A1 * | 2/2011 | Eaton et al. ....................... | 710/8 |
| 2011/0152629 A1 * | 6/2011 | Eaton et al. ................... | 600/300 |

* cited by examiner

*Primary Examiner* — Hung Duong

(74) *Attorney, Agent, or Firm* — Kory D. Christensen; Stoel Rives LLP

(57) ABSTRACT

Patient monitoring systems can include a docking station and a display unit. The display unit can be coupled with the docking station or decoupled from the docking station. Some display units can include one or more actuators that aid in decoupling the display unit from the docking station that can be actuated while the display unit is being gripped.

55 Claims, 21 Drawing Sheets

DISPLAY UNITS FOR USE IN MONITORING PATIENTS AND RELATED SYSTEMS AND METHODS

CROSS-REFERENCE TO RELATED APPLICATIONS

This application claims the benefit under 35 U.S.C. §119 (e) of pending U.S. Provisional Patent Application No. 61/236,798, titled DISPLAY UNITS FOR USE IN MONITORING PATIENTS AND RELATED SYSTEMS AND METHODS, filed on Aug. 25, 2009, the entire contents of which are hereby incorporated by reference herein.

TECHNICAL FIELD

The present disclosure relates to display units for use in monitoring patients.

SUMMARY

Embodiments of display units for use in monitoring patients, as well as related systems and methods, are disclosed.

DETAILED DESCRIPTION

Described herein are embodiments of display units for use in monitoring patients, as well as related systems and methods for their use. In some embodiments, a display unit is configured to be coupled with and decoupled from a docking station, which itself can be mounted in a hospital room or similar environment. The display unit can include features that simplify its connection to the docking station and/or features that simplify its disconnection from the docking station. Such connection and disconnection features can be particularly advantageous when the display unit, which can be heavy in some cases, is to interface with a docking station that is relatively difficult to access. For example, the docking station may be mounted in a high position that would require a medical practitioner to reach upwardly for access, and/or in a position above obstructions that would prevent a medical practitioner from standing at least partially below the docking station.

Figure 1:
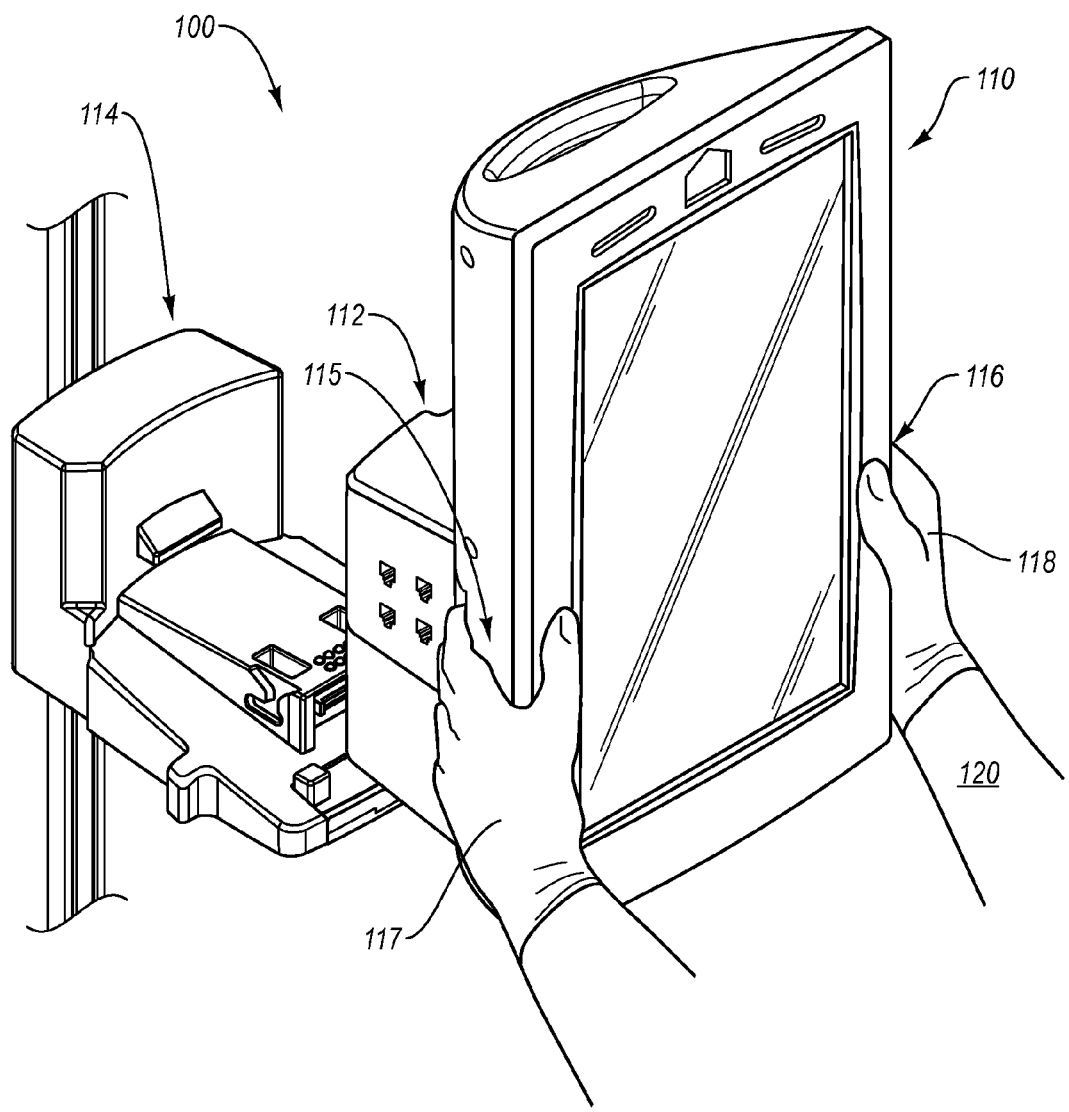
FIG. 1 is a front perspective view of an embodiment of a patient monitoring system in which an embodiment of a display unit is separated from an embodiment of a docking station and in which an embodiment of a patient parameter module is coupled with the display unit.

With reference to FIG. 1, in certain embodiments, a display system or a patient monitoring system 100 comprises a display unit 110, a patient parameter module 112, and a docking station 114. The display unit 110 can be configured to selectively couple with and decouple from the docking station 114, and the patient parameter module 112 can be configured to selectively couple with and decouple from the display unit 110. The coupling between the display unit 110 and the docking station 114, or between the patient parameter module and the display unit 110, can be mechanical, electrical, optical, and/or any other suitable variety. For example, the coupling can be for physical union, power transfer, and/or communication.

The display unit 110 can comprise one or more gripping regions 115, 116 (see also FIG. 12) that are configured to aid in coupling and decoupling the display unit 110 from the docking station 114. For example, a medical practitioner 120 can firmly grasp with his or her hands 117, 118 the gripping regions 115, 116 during removal of the display unit 110 from the docking station 114. When the display unit 110 is separated from the docking station 114, the full weight of the display unit 110 can be supported by a grip of the medical practitioner 120 on the gripping regions 115, 116. In some embodiments, the medical practitioner 120 can bear the full weight of the display unit 110 by holding only one of the gripping regions 115, 116.

The patient monitoring system 100 can comprise one or more actuators 122, 124 (see, e.g., FIG. 4) which, when actuated, permit release of the display unit 110 from the docking station 114. The actuators 122, 124 can be integrated into the gripping regions 115, 116 or other portions of the display unit 110 so as to permit for convenient and continuous-movement dismounting of the display unit 110. For example, in some embodiments, a practitioner 120 can actuate an actuator 122, 124 using a hand 117, 118 while that hand 117, 118 is simultaneously holding a respective gripping region 115, 116. These and other features of embodiments of the system 100 are described in further detail hereafter.

Figure 2:
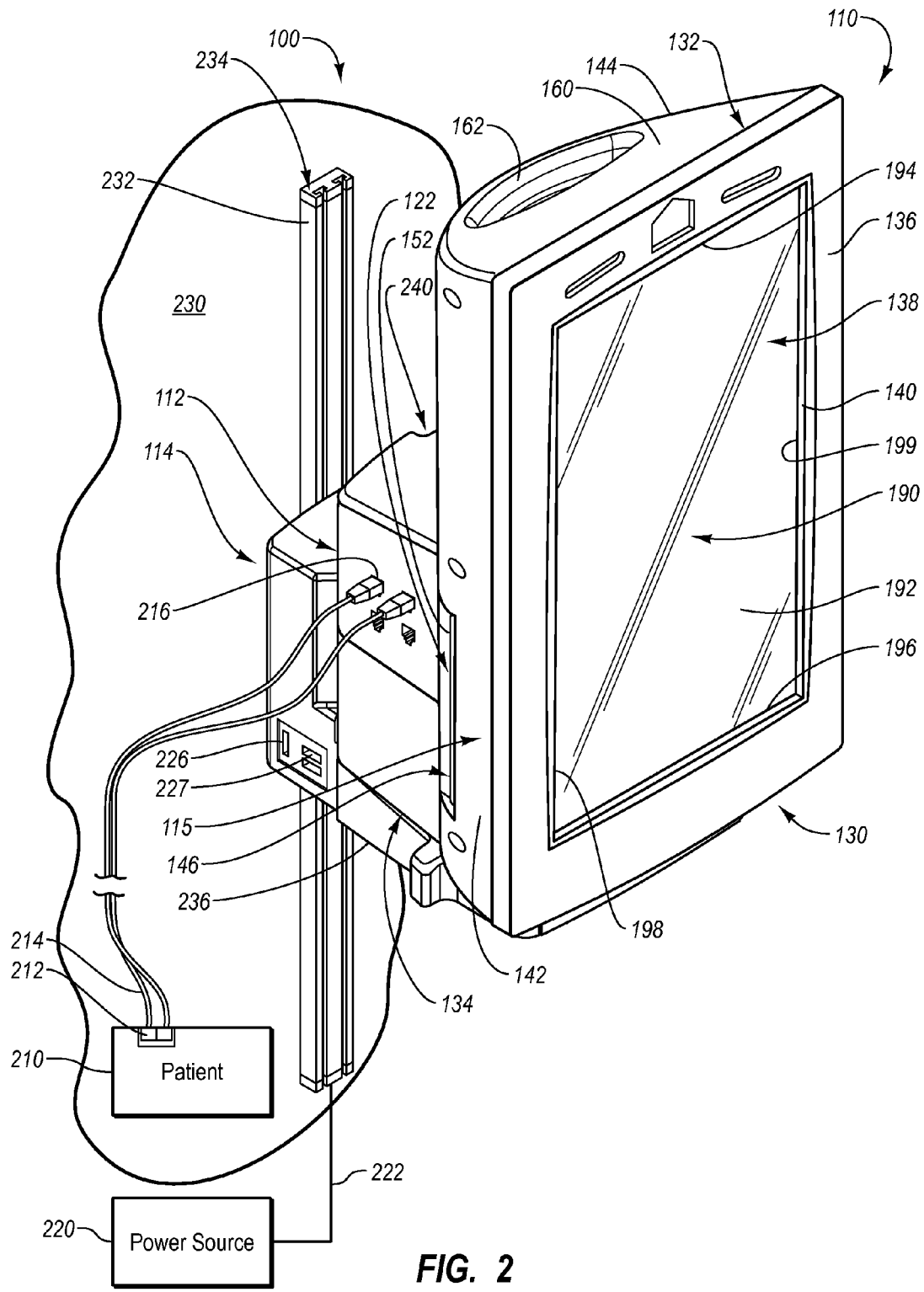
FIG. 2 is a front perspective view of the patient monitoring system of FIG. 1 in which the docking station is mounted to a wall and the display unit is coupled with the docking station and in which the patient parameter module is coupled with the display unit.
Figure 3:
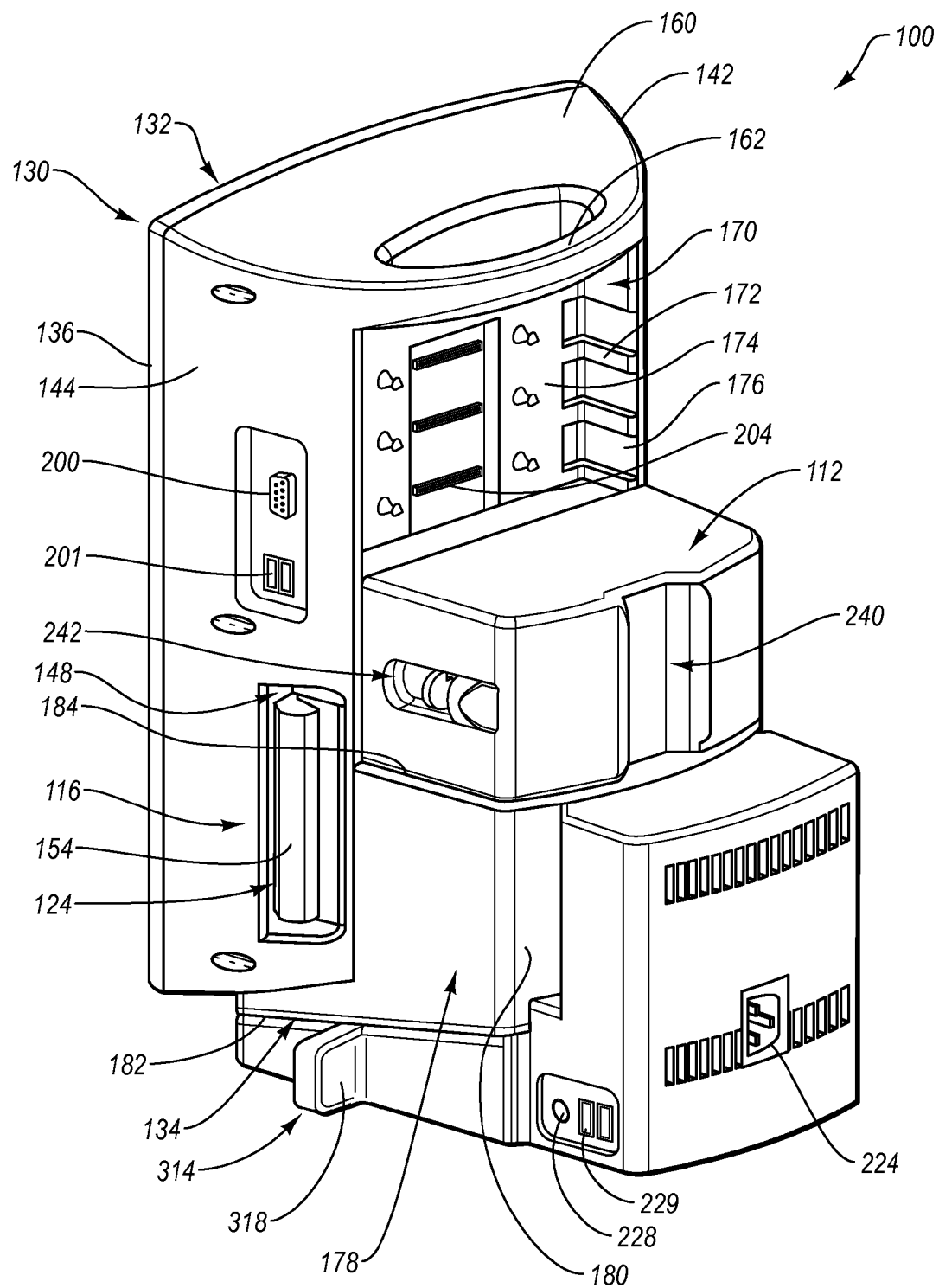
FIG. 3 is a rear perspective view of the patient monitoring system of FIG. 1 in which the display unit is coupled with the docking station and in which the patient parameter module is coupled with the display unit.

FIGS. 2 and 3 illustrate front and rear perspective views, respectively, of an embodiment of the system 100 in which the display unit 110 and the docking station 114 are in a coupled configuration, and in which the display unit 110 and the patient parameter module 112 are in a coupled configuration. Portions of the illustrated embodiment that are identifiable in this arrangement will now be described.

The display unit 110, which can also be referred to as a monitor or a display and control unit, comprises a housing 130. The housing 130 defines an upper end 132 and a lower end 134. Extending downwardly from the upper end 132 is a front face 136. In the illustrated embodiment, the front face 136 is substantially rectangular, and defines an opening 138. Surfaces of the housing 130 can extend rearward from the front face 136 around at least a portion of the perimeter of the opening 138 to define a rim 140.

The housing 130 can extend rearward from an outer edge of the front face 136. In the illustrated embodiment, a left side face 142 and a right side face 144 each extend rearward from the front face 136. The left and right side faces 142, 144 also extend inwardly towards a central longitudinal plane of the housing 130 so as to be substantially hidden from view from a vantage point directly in front of the front face 136 of the housing 130. Each of the left and right side faces 142, 144 can substantially resemble a portion of a cylinder.

As used herein, terms describing the orientation of an object, such as left, right, upper, lower, front, rear, etc. are recited from a perspective looking toward the front face 136 of the illustrated embodiment of the display unit 110, such as the perspective shown in FIG. 2. Such directional terms are used for convenience and should not necessarily be construed as limiting.

With continued reference to FIGS. 2 and 3, a left recess 146 extends from the left side face 142 toward an interior of the housing 130, and a right recess 148 extends from the right side face 144 toward the interior of the housing 130. Each of the left and right recesses 146, 148 can provide protection to a left actuator 122 and a right actuator 124, respectively. For example, in the illustrated embodiment, the left actuator 122 comprises a left handle 152 and the right actuator 124 comprises a right handle 154. The recesses 146, 148 can be sufficiently deep to permit the handles 152, 154 to be flush with, or recessed from, the side faces 142, 144 of the housing 130. Such positioning can prevent or impede accidental actuation of the actuators 122, 124. Likewise, as discussed below with respect to FIG. 12, the recesses 146, 148 can aid in providing structure to the gripping regions 115, 116 that is well-suited for grasping.

A top face 160 of the housing 130 can extend rearward from the front face 136. In the illustrated embodiment, the housing 130 defines a handle 162 that extends rearward and inwardly from the top face 160 and the left and right side faces 142, 144.

As shown in FIG. 3, the housing 130 can define a module cavity 170 configured to receive at least a portion of one or more patient parameter modules 112. Sidewalls 172 and a base wall 174 of the module cavity 170 can include grooves 176 that are complementary to protrusions (not shown) of a patient parameter module 112. The grooves 176 can facilitate coupling of the patient parameter module 112 with the display unit 110.

The housing 130 can define a rearward projection or base 178. The base 178 can extend inwardly and rearward from the left and right side faces 142, 144, and can terminate in a rearward end 180 (see also FIG. 4). The base 178 can include a substantially planar bottom face 182 (see also FIG. 4) and a substantially planar top face 184 (see also FIG. 7), and can resemble a trapezoidal prism.

With reference again to FIG. 2, a front surface of the display unit 110 can include a viewing area 190 that is configured to display information in a visually perceivable format. For example, the viewing area 190 can include a screen 192 of any suitable variety, including those presently known and those yet to be devised. For example, the screen 192 can comprise a liquid crystal display (LCD) panel. In some embodiments, the screen 192 can be configured to receive information or otherwise interact with a medical practitioner. For example, the screen 192 can comprise a touch screen.

In some embodiments, the screen 192 is configured to display information in a predetermined orientation that correlates with a docking orientation of the display unit 110. For example, in the illustrated embodiment, the screen 192 defines an upper end 194 and a lower end 196, and the upper end 194 is situated above or higher than the lower end 196 when the display unit 110 is coupled with the docking station 114. The screen can include side edges 198, 199 that extend between the upper and lower ends 194, 196. Information can be displayed on the screen 192 in an upright orientation when the display unit 110 is coupled with the docking station 114. For example, in the configuration depicted in FIG. 2, text, graphs, or other information can be displayed via the screen 192 in an orientation that is natural for reading.

As shown in FIG. 3, the display unit 110 can include one or more ports 200, 201 for receiving or delivering information, which can include one or more serial ports, USB ports, Ethernet ports, DVI ports, or any other suitable variety of ports, interfaces, or connectors. In some embodiments, information received via one or more of the ports 200, 201 can be displayed on the screen 192.

The display unit 110 can include one or more module connectors 204. The module connectors 204 can be configured to couple with complementary connectors (not shown)

on the patient parameter module 112 so as to permit communication between the patient parameter module 112 and the display unit 110.

With reference again to FIG. 2, at least a portion of the information displayed by the display unit 110 can represent information received from a patient 210 or that otherwise relates to the patient 210. For example, in some embodiments, one or more sensors 212 are connected to the patient 210 to sense a particular parameter, and information obtained via the one or more sensors 212 is delivered to the patient parameter module 112. In the illustrated embodiment, the sensors 212 deliver information to the patient parameter module 112 via one or more cables 214 connected to one or more ports 216. As with the ports 200, 201, the ports 216 can comprise any suitable variety of ports, interfaces, or connectors.

The patient parameter module 112 can be configured to process the information it receives from a sensor 212 and deliver it to the display unit 110, which can display the processed information. In some embodiments, the display unit 110 can further process the information prior to displaying it. The display unit 110 can also display information that is independent of the patient, such as, for example, a coordinate system or an interactive dialogue box.

As discussed further below, the display unit 110 can be configured to both mechanically and electrically couple with the docking station 114. The display unit 110 can receive power from the docking station 114, which itself can receive power from a power source 220 via a power line or cord 222. The power source 220 can comprise, for example, the AC wiring of a hospital. As shown in FIG. 3, the docking station 114 can include a socket 224 for coupling with a power cord 222.

With reference to FIGS. 2 and 3, the docking station 114 can comprise one or more ports 226, 227, 228, 229 for receiving or delivering information. As with the ports 200, 201, and 216, the ports 226, 227, 228, 229 can comprise any suitable variety of ports, interfaces, or connectors. As further discussed below, the docking station 114 and display unit 110 can be coupled so as to communicate with each other such that information received via one or more of the ports 226, 227, 228, 229 can be delivered to the display unit 110. Likewise, the display unit 110 can transmit information via one or more of the ports 226, 227, 228, 229. At least one of the ports 226, 227, 228, 229 can be configured to interface with a hospital network.

With reference again to FIG. 2, the docking station 114 can be mounted in a substantially fixed position. For example, the docking station 114 can be fixedly mounted to a wall within a hospital room in a single position by one or more plates, brackets, screws, bolts, or other mounting hardware and attachment devices. As another example, the docking station 114 can be configured to transition among multiple fixed positions. For example, in the illustrated embodiment, the docking station 114 is coupled to a mounting strip 232, which is in turn mounted to a wall 230 of a hospital room. The docking station 114 is capable of being adjusted upwardly or downwardly along a path constrained by one or more channels 234 defined by the mounting strip 232 so as to transition among a variety of positions. In each such position, the docking station 114 can be fixed relative to the mounting strip 232. In some embodiments, the docking station 114 is coupled with the mounting strip 232 via a mounting plate or a mounting bracket (not shown), the position of which can be adjusted upwardly or downwardly within the channels 234 in any suitable manner.

In other embodiments, the docking station 114 can be secured to a hospital bed (not shown), a mechanical arm (not shown), or any other suitable object. In some embodiments, a bottom surface 236 of the docking station 114 is positioned at a height of from about five feet to about six feet above a floor of a hospital room so as to allow the display unit 110 to be viewed easily and/or to avoid interference with other objects in the room.

With reference to FIGS. 2 and 3, the patient parameter module 112 can define a channel 240 extending longitudinally between an upper and lower face of the module 112. As shown in FIG. 3, the patient parameter module 112 can include a latch 242 that is configured to selectively secure the patient parameter module 112 to the display unit 110 and selectively release the patient parameter module 112 from the display unit 110. For example, the patient parameter module 112 can be moved forwardly into connection with the display unit 110 and secured in place by the latch 242. Conversely, the latch 242 can be actuated to release the patient parameter module 112 from the display unit 110. In the illustrated embodiment, the latch 242 is configured to be actuated in a direction that is substantially perpendicular to a longitudinal axis of the channel 240. Once released, the patient parameter module 112 can be moved rearward and then upwardly and/or outwardly between the wall 230 and the upper portion of the display unit 110.

In some embodiments, the latch 242 and/or the channel 240 can aid in single-handed coupling of the module 112 to the display unit 110. For example, in the embodiment illustrated in FIG. 3, a practitioner standing in front of or toward the right side of the patient monitoring system 100 can use his or her right hand to effectuate release of the module 112 from the display unit 110. One or more fingers or fingertips of the right hand can be inserted into the channel 240, and can grip against a right-facing surface of the channel 240. The thumb of the right hand can be positioned on the latch 242, and can move the latch 242 rearward to permit release of the module 112 from the display unit 110. The module 112 can then be urged rearward. The procedure can be reversed to couple the module 112 with the display unit 110. In other or further embodiments, the latch 242 can be positioned at the left side of the module 112, and a user's left hand can be used to couple and decouple the module 112 to and from the display unit 110 in a similar manner.

Figure 4:
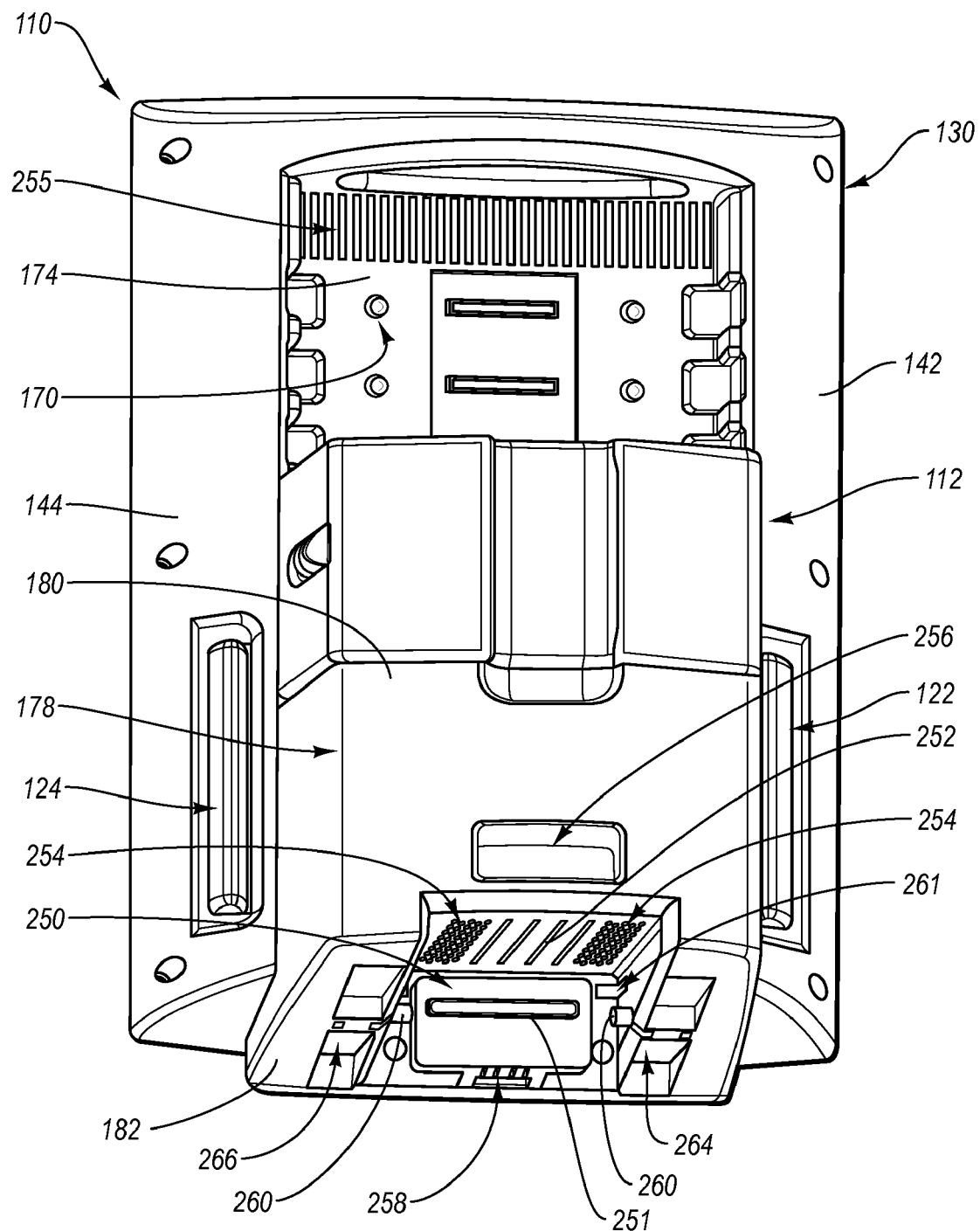
FIG. 4 is a rear perspective view of the display unit and patient parameter module of FIG. 1 showing a bottom region of the display unit.

FIG. 4 illustrates a bottom perspective view of a backside of the display unit 110. The display unit 110 is shown dismounted from the docking station 114 and coupled with the patient parameter module 112. In the illustrated embodiment, the housing 130 defines a docking cavity 250 configured to receive a portion of the docking station 114. At a front wall of the docking cavity 250, the display unit 110 includes a substantially rearward-facing communication port 251. The communication port 251 can comprise any suitable connector, and can be configured to receive power from and/or to communicate with the docking station 114. For example, in the illustrated embodiment, the communication port 251 comprises an electrical connector via which electrical power is transferred to the display unit 110 and via which electrical communications are transmitted between the display unit 110 and docking station 114. The communication port 251 can be configured to receive direct current at two separate voltages, such as, for example, at about 3 volts and at about 5 volts. Various other voltages and arrangements are possible.

The illustrated display unit 110 includes four electrical contact strips 252 in a top wall of the docking cavity 250 that are configured to receive direct current from the docking station 114 at two separate voltages. One pair of contact strips 252 is configured to operate at about 12 volts, and another pair of contact strips 252 is configured to operate at about 15 volts. Various other voltages and arrangements are possible.

The display unit 110 can include one or more venting regions 254, 255 to aid in dissipating heat generated by electrical components within the housing 130. In the illustrated embodiment, two venting regions 254 are disposed in the top wall of the docking cavity 250, and a venting region 255 is disposed in an upper end of the base wall 174 of the module cavity 170.

One or more alignment posts 260 can extend inwardly from side walls of the docking cavity 250 toward an interior of the docking cavity 250. In the illustrated embodiment, the alignment posts 260 are substantially aligned with each other so as to extend toward one another.

In the illustrated embodiment, a rearward locking recess 256 extends forwardly from the rearward end 180 of the housing 130 toward the interior of the housing 130. A forward locking recess 258 extends upwardly from the bottom face 182 of the housing 130 toward the interior of the housing 130. When the display unit 110 is coupled with the docking station 114, a bottom face (not shown) of the rearward locking recess 256 can be substantially horizontal and a rearward face (not shown) of the forward locking recess 258 can be substantially vertical.

A left dismount aperture 261 extends through a portion of each of the front wall and a left side wall of the docking cavity 250. Similarly, a right dismount aperture 262 (see FIG. 9) extends through a portion of each of the front wall and a right side wall of the docking cavity 250. As discussed below, the left and right dismount apertures 260, 262 can be sized and positioned to permit a portion of the left and right actuators 122, 124, respectively, to pass therethrough. A left plunger aperture 264 and a right plunger aperture 266 each extend through the bottom face 182 of the housing 130.

Figure 5:
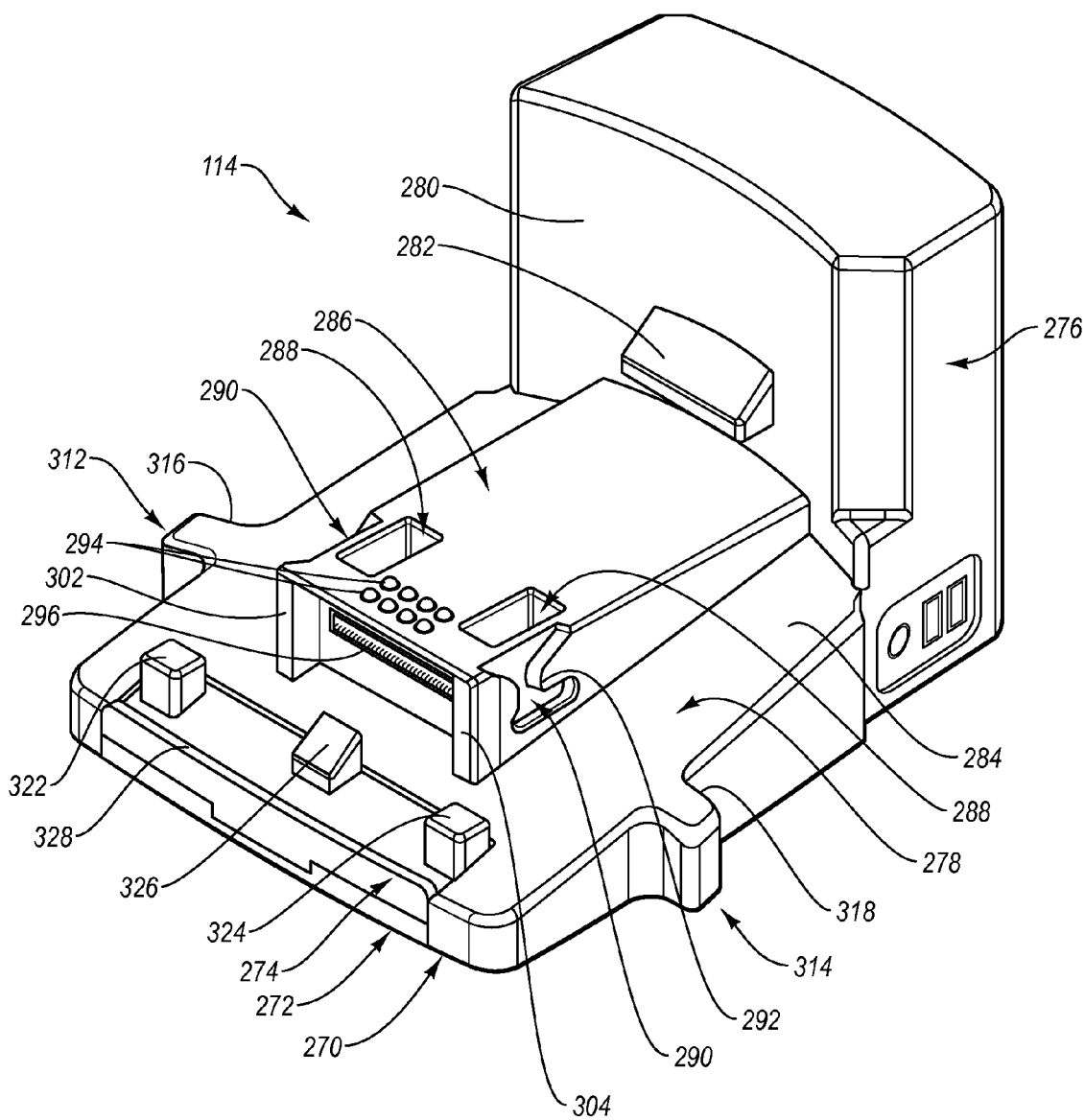
FIG. 5 is a front perspective view of the docking station of FIG. 1.
Figure 6:
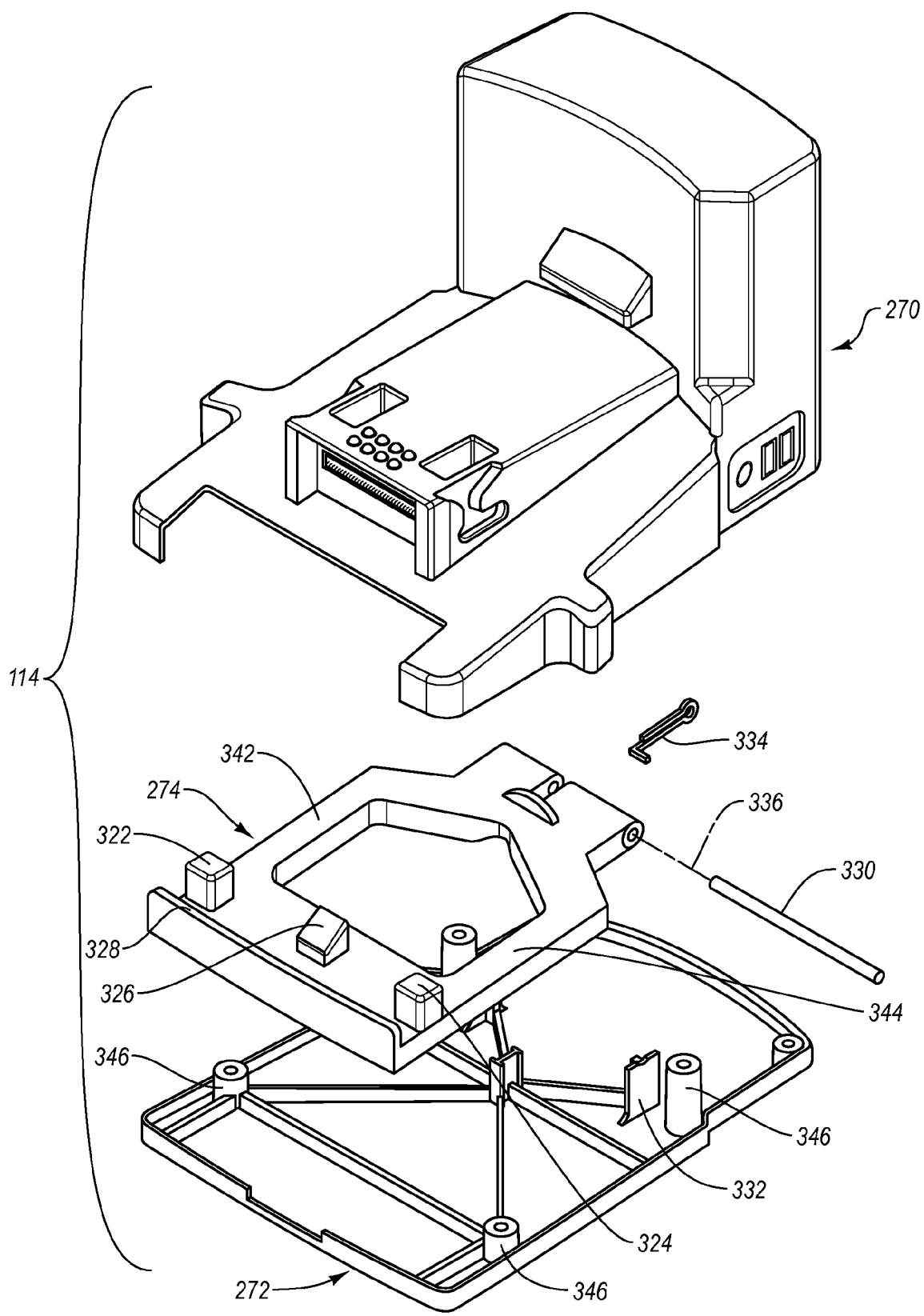
FIG. 6 is an exploded front perspective view of the docking station of FIG. 1.

FIG. 5 illustrates a perspective view of the docking station 114 when the docking station 114 and display unit 110 are in a decoupled configuration. FIG. 6 illustrates an exploded view of the docking station 114. As shown in FIGS. 5 and 6, the docking station 114 can comprise an upper housing 270, a lower housing 272, and a latch 274.

With reference to FIG. 5, the upper housing 270 can define a component tower 276 and a base 278. The component tower 276 can be shaped substantially as a parallelepiped, and can define an interior cavity (not shown) in which electrical components can be mounted. A front face 280 of the component tower 276 can be configured to contact the rearward end 180 of the housing 130 of the display unit 110. The front face 280 can include a rearward locking projection 282 that extends forwardly and is configured to be received within the rearward locking recess 256 of the display unit 110. A bottom face (not shown) of the rearward locking projection 282 can interfere with the bottom face (not shown) of the rearward locking recess 256 when the display unit 110 and docking station 114 are coupled to aid in maintaining the display unit 110 and docking station 114 in the coupled configuration.

The base 278 can be substantially wedge-shaped, and can increase in thickness from a front end toward a back end thereof. A lower surface 284 of the base 278 can be substantially planar, and can be substantially complementary to the bottom face 182 of the display unit 110. A substantially wedge-shaped peninsula, ledge, or docking interface 286 can extend upwardly from the lower surface 284 of the base 278. The docking interface 286 can define one or more venting apertures 288 through which air can pass into or out of the venting regions 254 of the display unit 110 when the display unit 110 and the docking station 114 are in the coupled configuration.

The docking interface 286 can define one or more alignment channels 290 that are configured to receive the one or more alignment posts 260 of the display unit 110. In the illustrated embodiment, the docking interface 286 defines two alignment channels 290 in opposing side walls. Each alignment channel 290 narrows from a wide opening at the top of a side wall to a neck 292 that is just large enough to allow passage of an alignment post 260 therethrough. Each channel 290 includes a lower region beneath the neck 292 sized to permit translation of an alignment post 260 therein, and which extends rearward relative to the neck 292.

The alignment channels 290 can aid in coupling the display unit 110 to the docking station 114. For example, the wide opening at the top of each channel 290 allows for relatively imprecise positioning of the display unit 110 relative to the docking station 114 at the outset of the coupling process. This can be advantageous when the docking station 114 is mounted in a high position such that a medical practitioner may exert a large force to heft the display unit 110 above the docking interface 286, and thus may not be able to immediately align the display unit 110 to the docking interface 286. The tapered sides of the channels 290 can guide the alignment posts 260 from a variety of starting positions downwardly into the lower regions of the channels 290, where the alignment posts 260 can then be urged rearward to lock the display unit 110 in place.

The docking interface 286 can include one or more rows of electrical contacts 294, which can be configured to provide power to the display unit 110 via the contact strips 252. In some embodiments, some of the electrical contacts 294 can provide the display unit 110 with direct current power at a voltage of about twelve volts, and others at a voltage of about fifteen volts. Various other voltages and arrangements are possible.

The docking interface 286 can include a substantially forward-facing communication port 296. The communication port 296 can comprise any suitable connector, and can be configured to deliver power to and/or to communicate with the display unit 110 via the communication port 251, as described above. The docking interface 286 can also define a left dismounting surface 302 and a right dismounting surface 304 at opposite sides of the communication port 296. The dismounting surfaces 302, 304 are discussed further below.

The base 278 of the upper housing 276 can define a left mounting grip 312 and a right mounting grip 314. The mounting grips 312, 314 comprise projections or protrusions that extend outwardly from sidewalls of the base 278. The left and right mounting grips 312, 314 can define rearward faces 316, 318 (see also FIG. 3), respectively, against which a medical practitioner can apply force to aid in coupling display unit 110 to the docking station 114. For example, in coupling the display unit 110 to the docking station 114, a medical practitioner can place the thumbs of both hands 117, 118 on the front face 136 of the display unit 110 and place at least a portion of one or more fingers on each of the rearward faces 316, 318, and can then push on the front face 136 and/or pull on the rearward faces 316, 318 to effect rearward movement of the display unit 110 relative to the docking station 114.

With reference to FIGS. 5 and 6, the latch 274 can include a left protrusion or plunger 322 and a right plunger 324 that extend upwardly. The left and right plungers 322, 324 can be sized and shaped to be received within the left and right plunger apertures 264, 266 of the display unit 110. The latch 274 can include a catch 326, which can be sized and shaped to be received within the forward locking recess 258 of the display unit 110. A rearward face (not shown) of the catch 326 can interfere with the rearward face (not shown) of the forward locking recess 258 when the display unit 110 and docking station 114 are coupled to aid in maintaining the display unit 110 and docking station 114 in the coupled configuration. The latch 274 can include a lip 328 configured to signal a coupling stage of the display unit 110 and the docking station 114, as further discussed below with respect to FIGS. 11A and 11B.

As shown in FIG. 6, the latch 274 can be mounted to the docking station 114 via a pin 330, which can be suspended via one or more holding posts 332. A biasing element 334, such as a torsion spring, can be positioned to provide a bias to the latch 274. For example, the biasing element 334 can be preloaded relative to the upper housing 270 or the lower housing 272 such that the latch 274 is biased upwardly toward a latched or locked configuration. One or more of the plungers 322, 324 can be displaced downwardly against the bias provided by the biasing element 334 to move the latch 274 into an unlatched or unlocked configuration.

In some embodiments, either plunger 322, 324 can be displaced downwardly into the unlocked configuration, even in the absence of any downward force being applied directly to the other plunger 322, 324. For example, in the illustrated embodiment, the latch 274 can include a left moment arm 342 and a right moment arm 344. The moment arms 342, 344 can be sufficiently long to provide for a large torque about an axis 336 defined by the pin 330 when either plunger 322, 324 is depressed.

Moreover, in some embodiments, movement of one plunger 322, 324 can also effect movement of the other plunger 322, 324. In the illustrated embodiment, the left and right plungers 322, 324, the catch 326, and the lip 328 are all integrally formed with the latch 274 as a unitary piece, and are configured to move in tandem. Accordingly, in the illustrated embodiment, downward displacement of a single plunger 322, 324 into an unlocked configuration can also move the other plunger 322, 324, as well as the catch 326, into an unlocked configuration.

The upper and lower housings 270, 272 can be attached to each other in any suitable manner. In the illustrated embodiment, a series of mounting posts 346 are employed.

Figure 7:
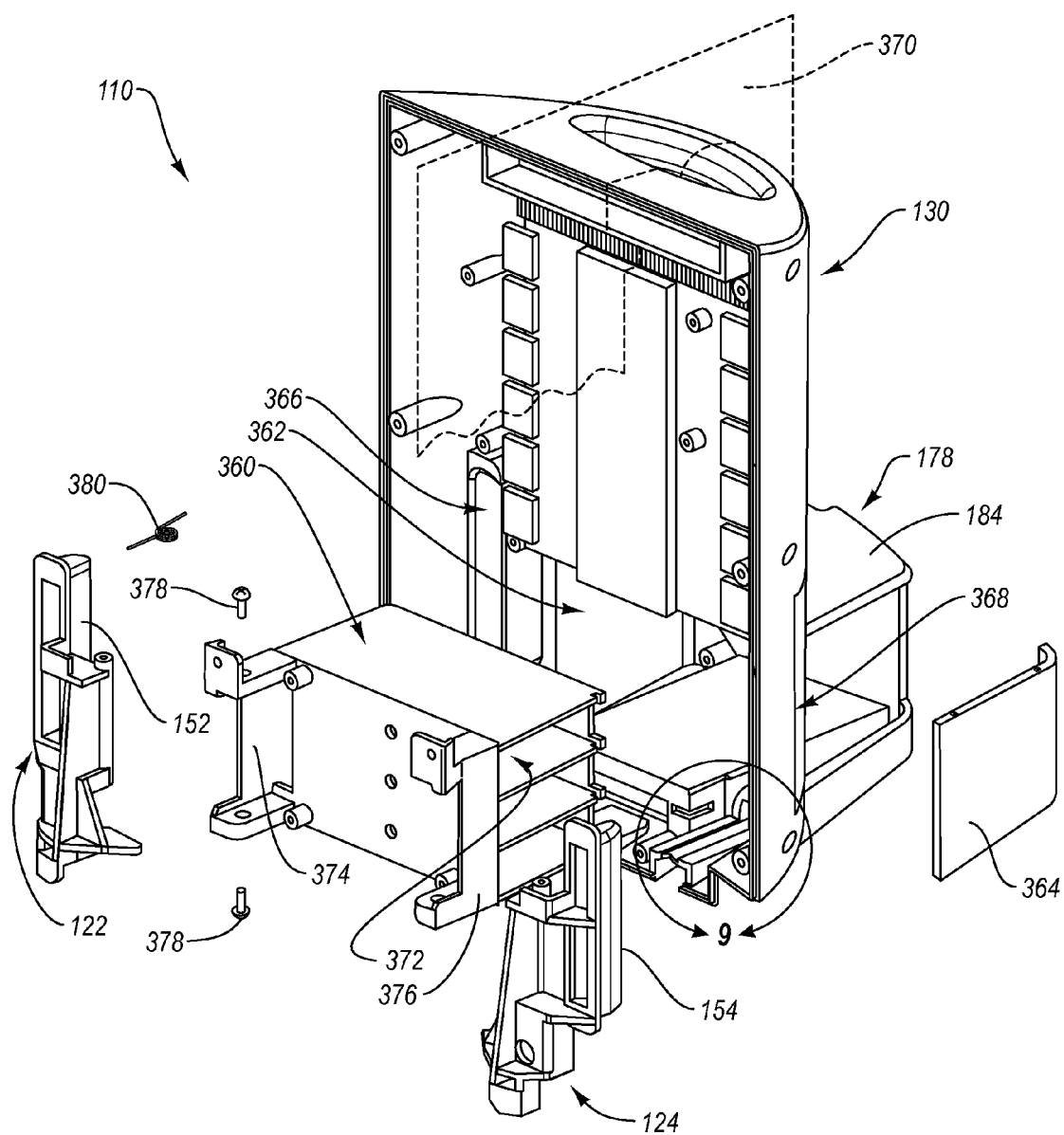
FIG. 7 is an exploded front perspective view of a portion of the display unit of FIG. 1.

FIG. 7 illustrates an exploded front perspective view of a portion of the display unit 110, including a rear segment of the housing 130, a chassis 360, and the left and right actuators 122, 124. Features not shown in FIG. 7 include a front segment of the housing 130 (which can comprise the front face 136), electrical components (such as the screen 192), and mounting hardware used to secure the front and rear segments of the housing 130, the electrical components, and the chassis 360.

The base 178 of the housing 130 can define a cavity 362 that is sized and dimensioned to receive at least a portion of the chassis 360 therein. The base 178 can include a removable cover 364, which can be selectively detached from the housing 130 to provide access to the cavity 362, or more particularly, to provide access to the chassis 360 when the display unit 110 is assembled.

The housing 130 can define a left handle opening 366 and a right handle opening 368 through which the left and right handles 152, 154, respectively, can extend. In the illustrated embodiment, the openings 366, 368 are elongated in a direction that is substantially parallel to a central longitudinal plane 370 of the housing 360, of which a top portion is depicted in FIG. 7.

The chassis 360 can define one or more receptacles 372, which can be sized and dimensioned to receive electrical components therein. For example, in the illustrated embodiment, the receptacles 372 can be configured to receive removable battery packs (not shown), and the battery packs can be selectively inserted or removed from the chassis 360 when the cover 364 is detached from the housing 360.

The chassis 360 can define a left mounting arm 374 and a right mounting arm 376 that extend forwardly. The left and right actuators 122, 124 can be attached to the mounting arms 374, 376 such that the actuators 122, 124 can rotate relative to the chassis 360 once mounted. Screws 378 used to attach the left actuator 122 to the left mounting arm 374 are shown. In some embodiments, the screws 378 comprise shoulder screws, as this term is understood in the art.

A biasing element can be used to bias an actuator 122, 124 to a natural, resting, deactivated, disengaged, or un-actuated position. For example, in the illustrated embodiment, a biasing element 380 is assembled with the left actuator 122 and the chassis 360 so as to bias the left actuator to rotate in a clockwise direction, as viewed from above. The left actuator 122 can be rotated in a counterclockwise direction against the bias provided by the biasing element 380 into an active, activated, engaged, or actuated position. A similar biasing element can be used with the right actuator 124 to provide a rotational bias in a counterclockwise direction, as viewed from above.

In the illustrated embodiment, the right and left actuators 122, 124 comprise substantially identical elements, but are substantially mirror-images of each other. The same is true for the bottom right and bottom left corners of the housing 130. Accordingly, the following discussion regarding the right actuator 124 and bottom right corner of the housing 130 can apply equally to the left actuator 124 and the bottom left corner of the housing 130, with the appropriate portions of the discussion reversed.

Figure 8:
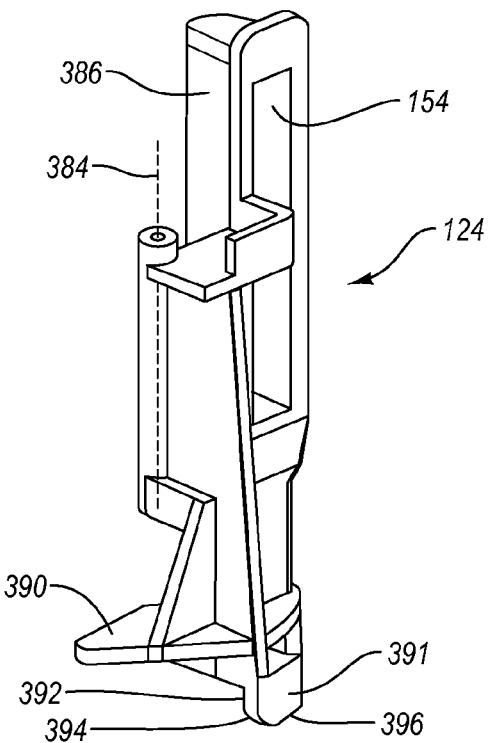
FIG. 8 is a perspective view of an embodiment of an actuator compatible with the patient monitoring system of FIG. 1.
Figure 9:
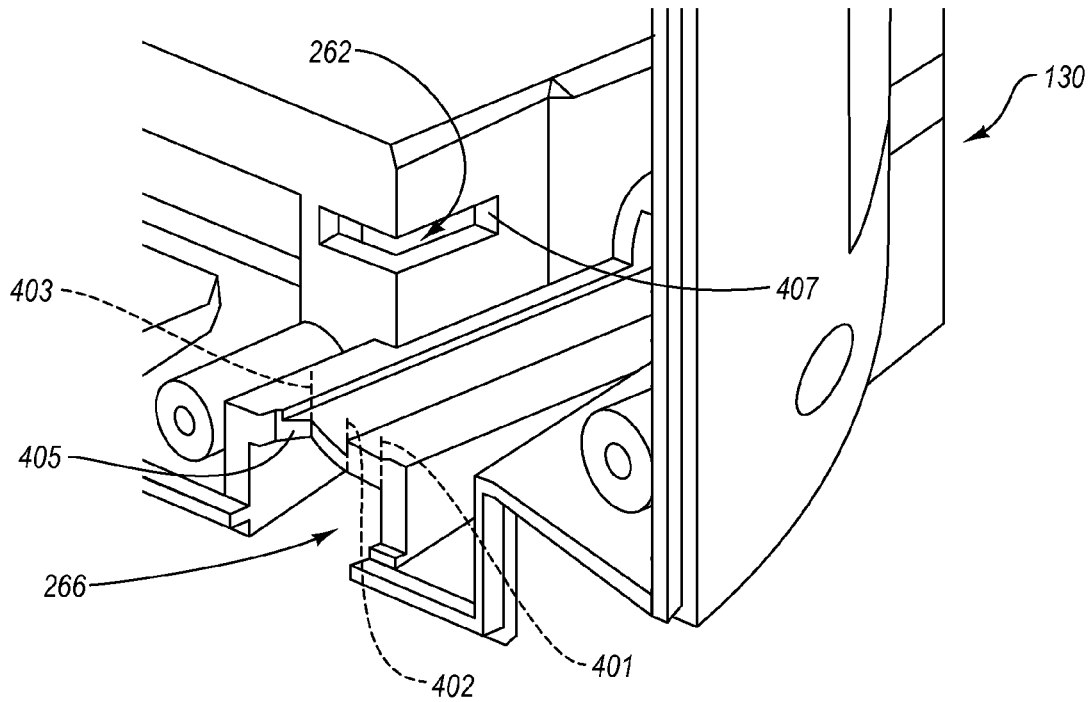
FIG. 9 is an enlarged front perspective view of an embodiment of a housing compatible with the display unit of FIG. 1.

FIG. 8 illustrates an enlarged front perspective view of the right actuator 124 rotated by about 90 degrees in a counterclockwise direction, as viewed from above, relative to the position shown in FIG. 7. FIG. 9 illustrates an enlarged front perspective view of a bottom right corner of the housing 130.

As shown in FIG. 8, the handle 154 can be elongated in a direction substantially parallel to an axis 384 about which the actuator 124 is configured to rotate. The handle 154 can include a finger grip or gripping surface 386 along its length that is configured to receive one or more fingertips of a medical practitioner thereon. In various embodiments, a length of the gripping surface 386 can be sufficient to receive thereon one or more, two or more, three or more, or four fingertips of a medical practitioner. In various embodiments, the length of the gripping surface 386 can be from about 0.5 inches to about 4.0 inches, from about 1.0 inches to about 3.0 inches, from about 1.0 inches to about 2.5 inches, no less than about 1.0 inches, no less than about 2.0 inches, no less than about 3.0 inches, no more than about 1.0 inches, no more than about 2.0 inches, or no more than about 3.0 inches.

The axis 384 can assume a variety of orientations when the actuator 124 is mounted within the housing 130. In the illustrated embodiment, the axis 384 is substantially parallel to the central longitudinal plane 370 of the housing 130 and substantially vertical when the actuator 124 is mounted in the housing 130.

The actuator 124 can comprise a dismount protrusion 390 and a bottom flange 391, which can be rotationally spaced from each other. In the illustrated embodiment, the dismount protrusion 390 and the bottom flange 391 are rotationally separated by about 90 degrees, although any other suitable arrangement is possible. The bottom flange 391 can include a leading surface 392, which can be substantially vertical. Sloping downwardly from the leading surface 392 and in a direction rotationally away from the dismount protrusion 390 is an actuation surface 394, which can be substantially rounded or angled. The actuation surface 394 can transition into a depression surface 396.

As shown in FIG. 9, the right dismount aperture 262 and the right plunger aperture 266 can be in relatively close proximity to each other. As discussed hereafter, portions of the actuator 124 can simultaneously extend into or through each aperture 262, 266, depending on the rotational orientation of the actuator 124.

When the display unit 110 is fully assembled and is connected to the docking station 114, the right plunger 324 (see FIG. 5) can extend into the right plunger aperture 266, and can be in the locked configuration described above. The actuator 124 can be biased toward a resting, starting, original, or un-actuated position 401. The vertical dashed line depicting the un-actuated position 401 signifies the position of the leading surface 392 of the bottom flange 391 of the actuator 124.

The actuator 124 can be rotated in a clockwise direction, as viewed from above, to an unlocking, unlatching, depression, or actuation orientation 402. As the actuator 124 is rotated to the actuation orientation 402, the actuation surface 394 of the actuator 124 contacts an upper surface of the right plunger 324, and the slope of the actuation surface 394 urges the plunger 324 downwardly into the unlocked configuration described above. Correspondingly, the catch 326 is moved out of the forward locking recess 258 of the display unit 110, and the left plunger 322 is moved out of the left plunger aperture 264 of the display unit 110 (see FIGS. 4 and 5). Thus, when the actuator 124 is in the actuation orientation 402, a medical practitioner can urge the display unit 110 forwardly to thereby disengage the communication ports 251, 296 (see FIGS. 4 and 5) and remove the display unit 110 from the docking station 114.

The illustrated embodiment provides for at least an additional orientation of the actuator 124 that can aid in separating the display unit 110 from the docking station 114. The actuator 124 can be rotated clockwise from the actuation orientation 402 into a separation or dismounted orientation 403. As the actuator 124 is rotated to the dismounted orientation 403, the depression surface 396 of the actuator 124 maintains the right plunger 324 in the unlatched configuration. Additionally, the dismount protrusion 390 passes through the right dismount aperture 262 into contact with the right dismounting surface 304 of the docking station 114 (see FIG. 5). Additional clockwise rotation of the actuator 124 causes the dismount protrusion 390 to press off of the dismounting surface 304 and urge the display unit 110 away from the docking station 114.

As previously mentioned, in the illustrated embodiment, displacement of either of the plungers 322, 324 can move the latch 274 into the unlocked configuration. Accordingly, in some embodiments, decoupling of the display unit 110 from the docking station 114 can be achieved by depressing only the right plunger 324 via the right actuator 124, as just described. Additionally, due to the symmetry of the illustrated embodiment, decoupling can be achieved by actuation of only the left actuator 122. Additionally, decoupling can be achieved by actuation of both actuators 122, 124. For example, simultaneous actuation of the actuators 122, 124 can effect movement of the latch 274 into the unlocked orientation.

Once the latch 274 has been unlocked, the display unit 110 can be moved forward relative to the docking station 114. The alignment posts 260 (see FIG. 4) thus can move forward within the channels 290 (see FIG. 5). Interaction between a front edge of each channel 290 and the alignment posts 260 can limit the forward movement of the docking station 114. Once the alignment posts 260 are positioned in a front region of the channels 290, the display unit 110 can be lifted upwardly and away from the docking station 114.

Figure 10:
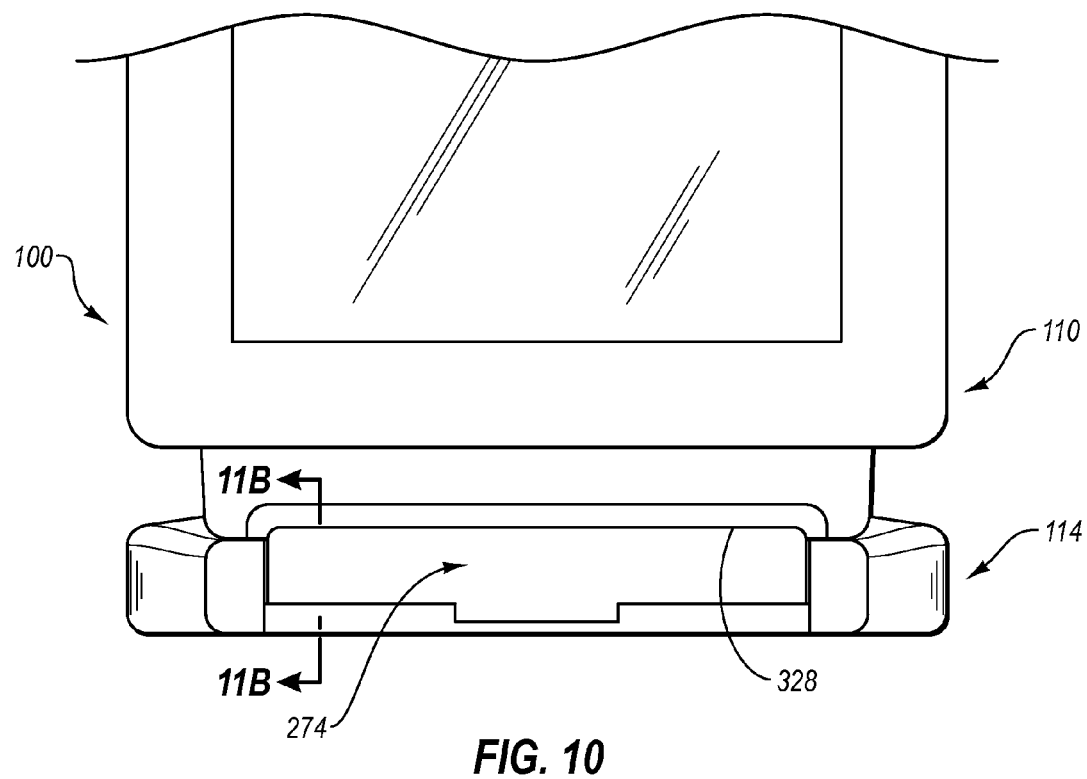
FIG. 10 is a front elevation view of a lower portion of the patient monitoring system of FIG. 1.
Figure 11A:
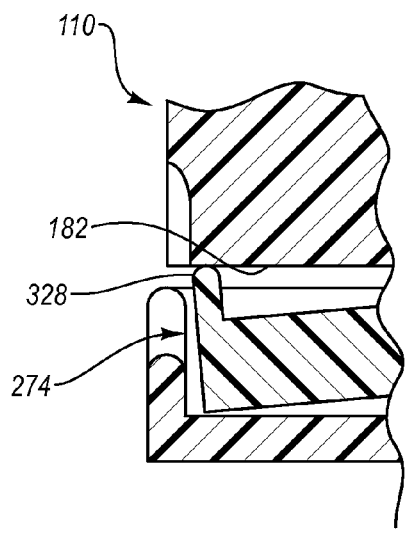
FIG. 11A is a cross-sectional view of a portion of the patient monitoring system of FIG. 1, taken along a view line such as the view line 11B-11B in FIG. 10, in which the display unit and docking station are in an uncoupled configuration.
Figure 11B:
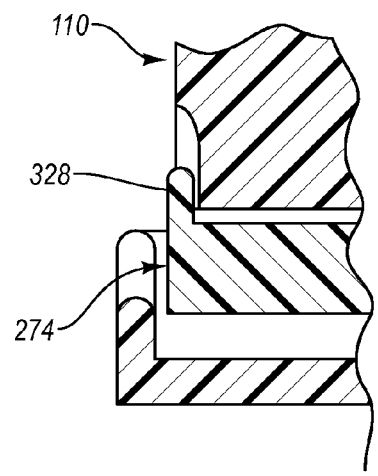
FIG. 11B is a cross-sectional view of a portion of the patient monitoring system of FIG. 1, taken along the view line 11B-11B in FIG. 10, in which the display unit and docking station are in a coupled configuration.

FIG. 10 illustrates a front plan view of an embodiment of the system 100 with the display unit 110 and the docking station 114 in a coupled configuration, which is also shown in cross-section in FIG. 11B. In contrast, FIG. 11A illustrates the display unit 110 just prior to achievement of coupling between the display unit 110 and the docking station 114. Comparison of FIGS. 11A and 11B illustrates that the lip 328 of the latch 274 can indicate the docking status of the display unit 110 and the docking station 114.

In particular, with reference to FIG. 11A, the latch 274 can be held in the unlocked orientation by the bottom face 182 of the display unit 110 when the display unit 110 and the docking station 114 are not fully coupled. As the display unit 110 is moved rearward to the position shown in FIG. 11B, the latch 274 can move upward into the locking orientation. In this orientation, the lip 328 can be in front of a portion of the display unit 110, obscuring it from view. Accordingly, the position of the lip 328 can provide a visual indication of whether the display unit 110 and the docking station 114 are fully coupled.

Figure 12:
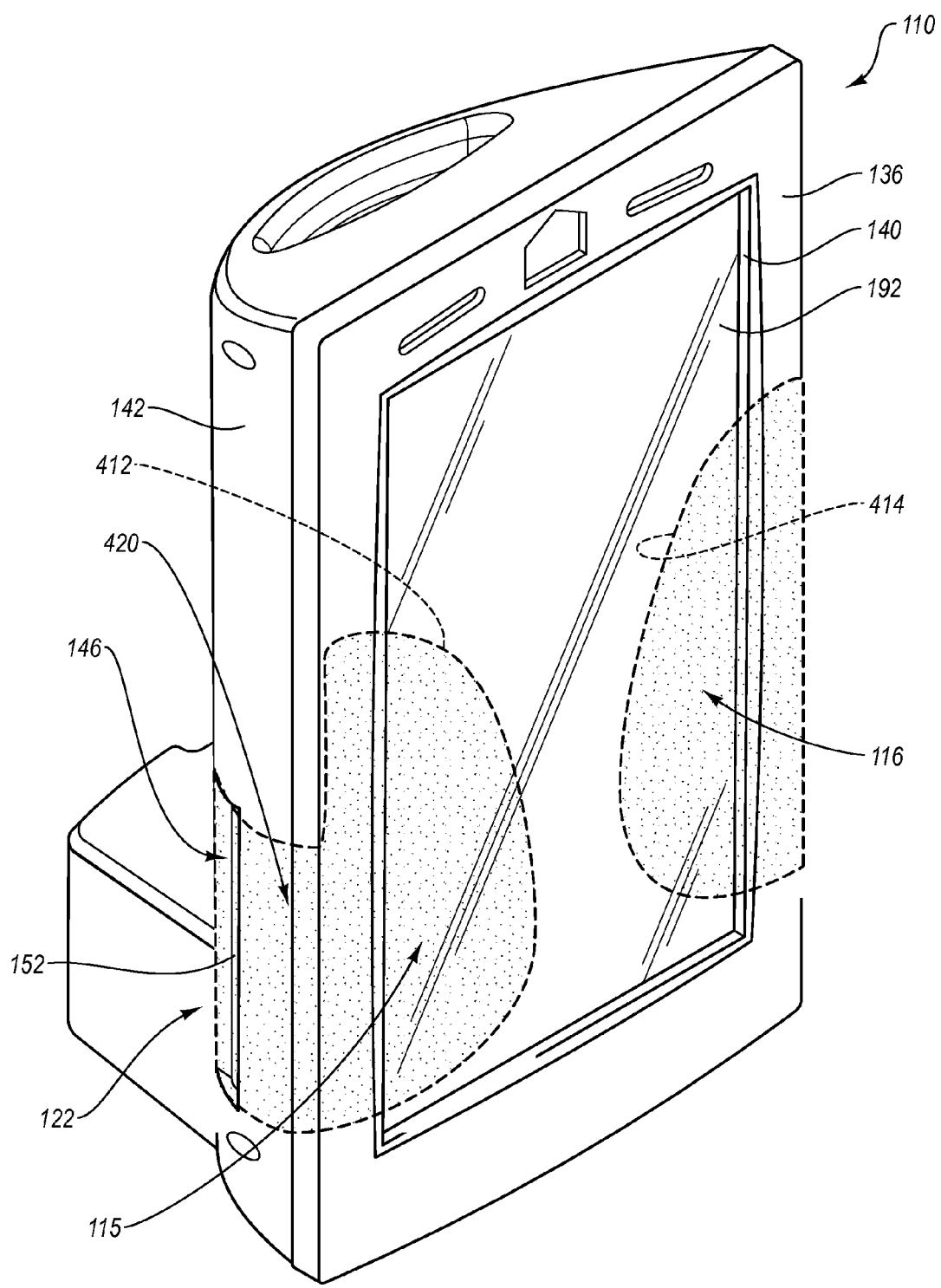
FIG. 12 is a front perspective view of another embodiment of a display unit illustrating an embodiment of gripping regions.

FIG. 12 illustrates an outer contour 412 of the left gripping region 115 and an outer contour 414 of the right gripping region 116 for an embodiment of the display unit 110. The left gripping region 115 can include portions of the screen 192, the rim 140, the front face 136, the left side face 142, and the actuator 122. The gripping region 115 can extend into the left recess 146, where a gripping surface 386 (see FIG. 8) of the left handle 152 is exposed. The right gripping region 116 can include similar portions of the right side of the display unit 100.

Due to the geometry and structure of the foregoing features, which are discussed in detail above, the gripping region 115 can define a substantially handle-shaped region 410 about which a fist, or partial fist, can be formed. For example, a medical practitioner can hold, grasp, grip, or clench the handle-shaped region 410 by curling, curving, bending, or tightening one, two, three, or four fingers of the left hand 117 around the left side face 142 and into the left recess 146. The palm of the left hand 117 can rest on the left side face 142 and/or on the front face 136. The thumb of the left hand can be placed in a variety of orientations, including extending upwardly along the front face 136, extending inwardly near a bottom edge of the screen 192, and extending at an angle to these positions. In some embodiments, the rim 140 can provide a convenient location for resting the thumb.

In some instances, by holding the handle-shaped region 420, a medical practitioner can support or bear the entire weight of the display unit 110. For example, the display unit 110 can be carried in a sideways or substantially horizontal orientation in which the screen 192 is lower than the portion of the left side face 142 within the gripping region 115. In some instances, by holding the handle-shaped region 420, a medical practitioner can support or bear at least a portion of the weight of the display unit 110, such as when the right hand 118 is simultaneously used to hold the right gripping region 116.

Other gripping arrangements are also possible. For example, rather than resting the palm on the display unit 110, the fingers of the left hand 117 can be placed on the handle 152 and the thumb can be placed on the left side face 142 within the gripping region 115. Pressure applied by the fingers and thumb in substantially opposite directions can provide sufficient force to bear some or all of the weight of the display unit 110.

The contour 412 of the gripping region 115, or at least a portion thereof, can be defined by the maximum distances that can be reached by a hand 117 of a given size while the hand 117 is maintaining a grip on the gripping region 115. Human hand sizes can be determined according to well-known practices. For example, surgical gloves often are manufactured according to standardized sizes such as extra-extra small (XXS), extra small (XS), small (S), medium (M), large (L), extra large (XL), extra-extra large (XXL), and extra-extra-extra large (XXXL). The foregoing sizing system is often used in the United States. Other glove sizing systems are also known. For example, in Europe, hand or glove sizes can include 6, 6.5, 7, 7.5, 8, 8.5, 9, 9.5, 10, 10.5, 11, 11.5, 12, 12.5, 13, 13.5, or larger. Relative dimensions for the palm, thumb, and fingers based on the foregoing sizing systems are known.

Other measurements are also commonly made to determine hand size. For example, knuckle girth can be determined by measuring the perimeter of the hand just below the knuckles while the fingers form a light fist, and finger length can be measured from the bottom edge of a palm to the tip of the middle finger. Knuckle girth of many adult humans can measure from about 6 inches to about 12 inches. Any subset of girths within this range is also possible, as are girths outside of this range. Common finger lengths can measure from about 5.5 inches to about 9 inches. Any subset of lengths within this range is also possible, as are lengths outside of this range.

The contour 412 of the gripping region, or at least a portion thereof, can be defined by an area reachable by a hand having one or more of any of the foregoing sizes, or that is within any of the foregoing measurement ranges (or subsets thereof), while the hand grasps the gripping region 115 in a manner that allows support of some or all of the weight of the display unit 110. Gripping regions can also be configured for human hands larger or smaller than those specifically described.

With continued reference to FIG. 12, the display unit 110 can be decoupled from the docking station 114 by holding the gripping region 115 with the left hand 117 and simultaneously actuating the left actuator 122 with the left hand 117. For example, as the left hand 117 grasps the gripping region 115, the fingers of the hand 117 can pull on the left handle 152 to effect actuation of the actuator 124. Stated differently, the actuator 122 can be actuated by tightening a grasp on the gripping region 115. For example, the actuator 122 can be moved from the un-actuated position 401 (FIG. 9) to the actuated position 402 (FIG. 9) as a medical practitioner tightens a grip on the gripping region 115 in a natural manner. The gripping region 115 can be held, the actuator 112 actuated, and the display unit 110 removed from the docking station 114 and subsequently supported as the gripping region is continuously grasped (e.g., without a hold or a grasp on the gripping region 115 being released).

Figure 13:
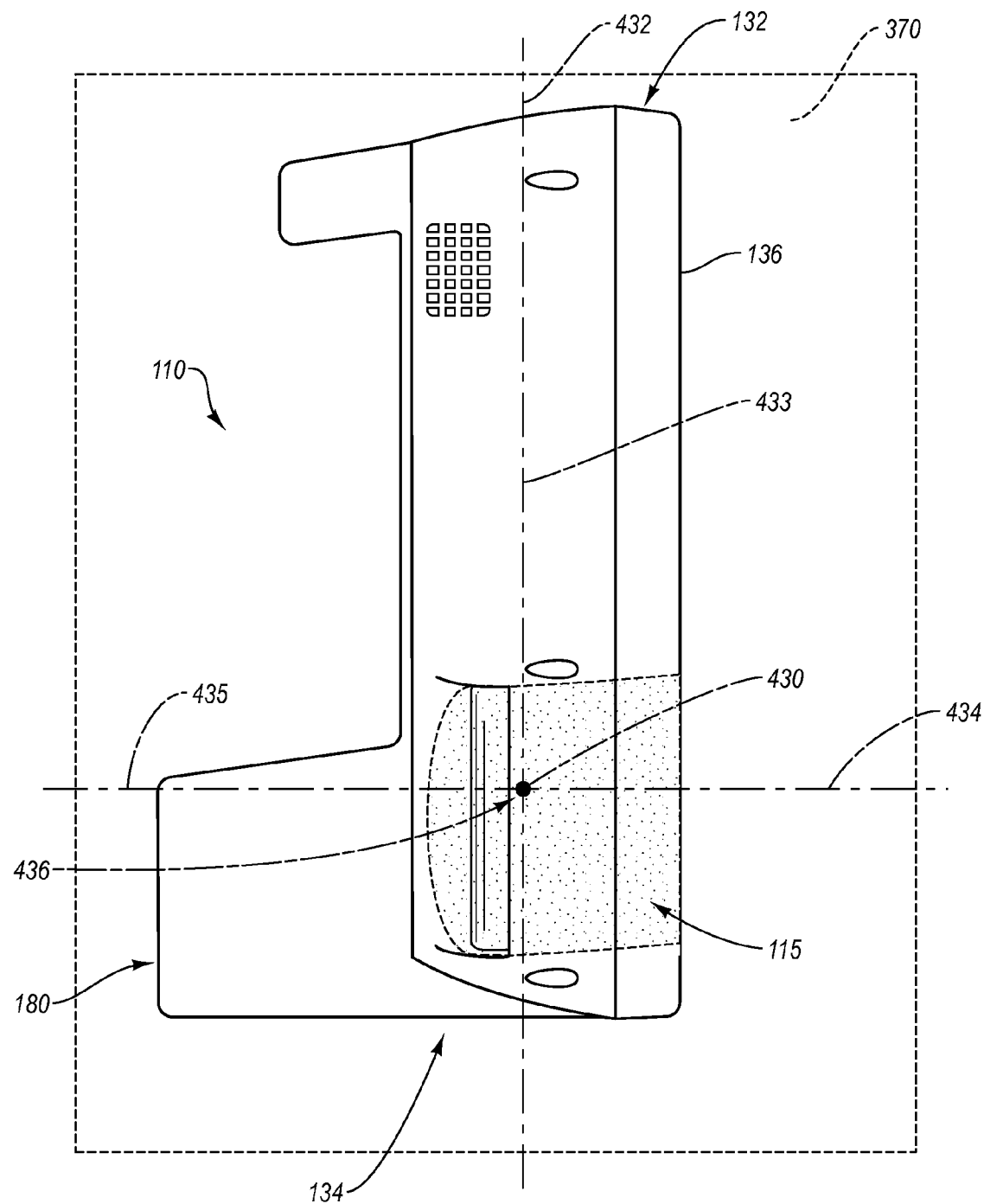
FIG. 13 is a side elevation view of another embodiment of a display unit illustrating the location of a center of gravity.

FIG. 13 illustrates a side elevation view of an embodiment of a display unit 110 that includes a center of gravity 430 at an interior thereof. In the illustrated embodiment, the center of gravity 430 is positioned at a meeting point of the central longitudinal plane 370, an orthogonal transverse plane 432, and an orthogonal lateral plane 434. The transverse plane 432 defines a transverse axis 433 along the intersection of the longitudinal and transverse planes 370, 432, and the lateral plane 434 defines a lateral axis 435 along the intersection of the longitudinal and lateral planes 370, 434. A lateral axis 436, which extends into and out of the page in the view shown in FIG. 3, can be defined at the intersection of the transverse and lateral planes 432, 434.

In some embodiments, the left gripping region 115 can be positioned relative to the center of gravity 430 such that rotational moments about one or more of the transverse and lateral axes 433, 435 are small or non-existent when the lateral plane 434 is substantially horizontal and the gripping region 115 is being held so as to support the full weight of the display unit 110. In some embodiments, the lateral axis 436 passes through both the center of gravity 430 and one or more of the left and right gripping regions 115, 116.

Figure 14:
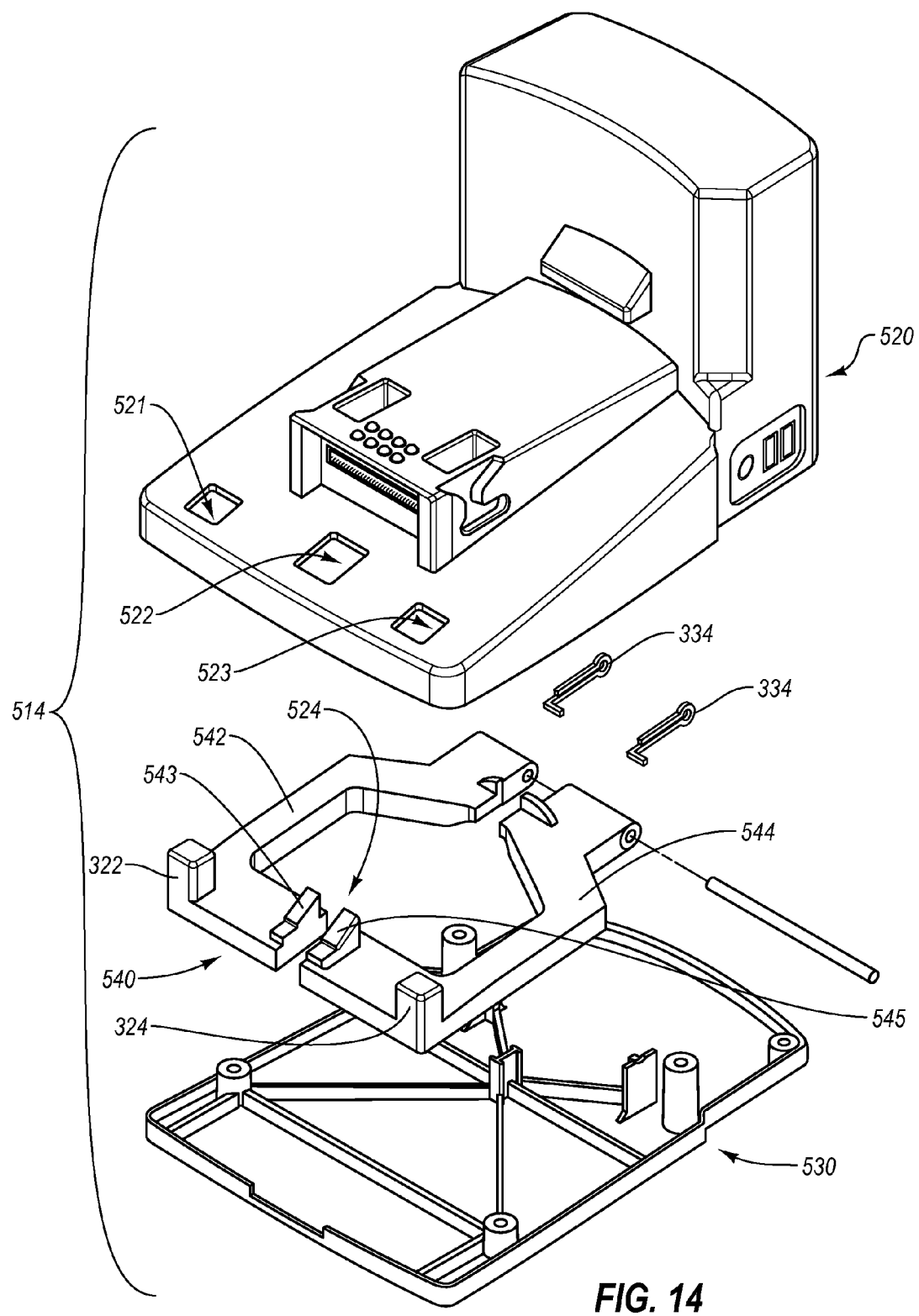
FIG. 14 is an exploded front perspective view of another embodiment of a docking station that includes a latch configuration different than that illustrated in FIG. 6.

FIG. 14 illustrates another embodiment of a docking station 514 compatible with embodiments of the system 100. The docking station 514 can resemble the docking station 114 in many respects, thus like features are identified with like reference numerals. The docking station 514 can require that both actuators 122, 124 be actuated in order to disengage the display unit 110 from the docking station 514. Actuation of one of the actuators 122, 124 can be time-delayed relative to actuation of the actuators 122, 124, or it can be simultaneous therewith.

The docking station 514 can include an upper housing 520 that defines a plurality of apertures 521, 522, 523 through which a left plunger 322, a catch 524, and a right plunger 324, respectively, can extend. In the illustrated embodiment, the upper housing 520 does not include mounting grips. In other embodiments, mounting grips 314, 316 can be included on the upper housing 520 or on a lower housing 530 (such as, for example, at a bottom surface of the lower housing 530).

The docking station 514 can include a latch 540. The latch 540 can comprise a left latch member 542, which can define a left catch member 543 and the left plunger 322, and can also comprise a right latch member 544, which can define a right catch member 545 and the right plunger 324. The left and right latch members 542, 544 are separate from each other and can be moved individually between locked and unlocked orientations. A separate biasing element 334 biases each latch member 542, 544 toward the respective locked orientation.

With both latch members 542, 544 in the locked orientation, the catch members 543, 545 extend through the aperture 522 and engage the display unit 110. Since displacement of either latch member 542, 544 into the unlocked orientation occurs independent of the orientation of the other latch member 542, 544, both latch members 542, 544 must be displaced into the unlocked orientation to allow decoupling of the display unit 110 from the docking station 514.

In the illustrated embodiment, both actuators 122, 124 must at some point in time simultaneously depress the left and right plungers 322, 324 to as to simultaneously clear the left and right catch members 543, 545 to thereby allow removal of the display unit 110 from the docking station 514. In other embodiments, one or more of the left and right latch members 542, 544 may include a mechanism that maintains the latch member in a depressed orientation once it has been displaced thereto. Thus, for example, actuating and releasing the left actuator 122 can clear the left catch member 543 and cause it to remain in a cleared state, and actuating and releasing the right actuator 124 can clear right catch member 545 and cause it to remain in a cleared state. In such a configuration, the left and right actuators 122, 124 can be actuated at different times, and once each has been actuated, the display unit 110 can be removed from the docking station 514. In certain of such embodiments, the left and right latch members 542, 544 may remain in a depressed state until the display unit 110 is once again joined to the docking station 514, at which point the mechanism may be reset so that the biasing elements 334 bias the latch members 542, 544 toward their respective locked orientations.

Figure 15:
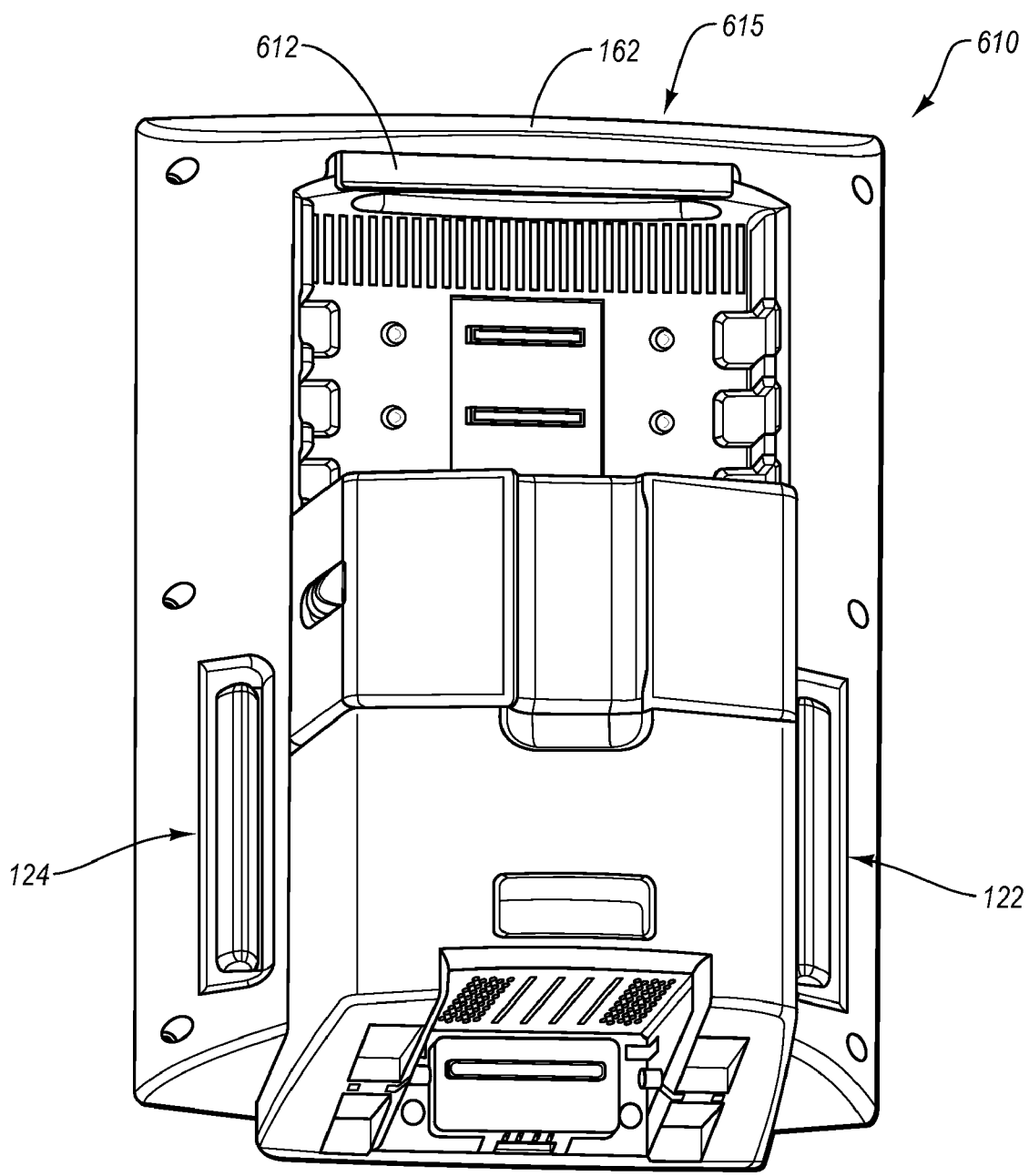
FIG. 15 is a rear perspective view of another embodiment of display unit that includes an embodiment of an actuator coupled to an embodiment of a handle.

FIG. 15 illustrates another embodiment of display unit 610 compatible with embodiments of the system 100. The display unit 610 can resemble the display unit 110 in many respects, thus like features are identified with like reference numerals. The display unit 110 can include an upper actuator 612 within its handle 162. In some embodiments, the upper actuator 612 is mechanically tied to one or more of the actuators 122, 124 such that actuation of the upper actuator 612 effects actuation of one or both of the actuators 122, 124. For example, in some embodiments, the upper actuator 612 is mechanically tied to the left actuator 122 only, and the display unit 610 is coupled with a docking station (e.g., the docking station 514). In certain of such embodiments, actuation of the right actuator 124, along with (whether separately or simultaneously) one of the upper actuator 612 and the left actuator 122, may be required to effect disengagement of the display unit 610 from the docking station 514. In other embodiments, the upper actuator 612 is mechanically tied to both actuators 122, 124. In certain of such embodiments, a user can either actuate the side actuators 122, 124 (whether separately or simultaneously) or only the upper actuator 612 in order to decouple the display unit 610 from a docking station. In still other embodiments, a user may be required to actuate all three actuators 122, 124, 612 in order to effect a decoupling. Other combinations of the actuators 122, 124, 612 are possible. In still other embodiments, the display unit 610 includes only the upper actuator 612.

In certain embodiments, the display unit 610 can comprise a gripping region 615 that extends substantially along a length of the handle. The gripping region 615 can include an exposed surface of the upper actuator 612.

Figure 16:
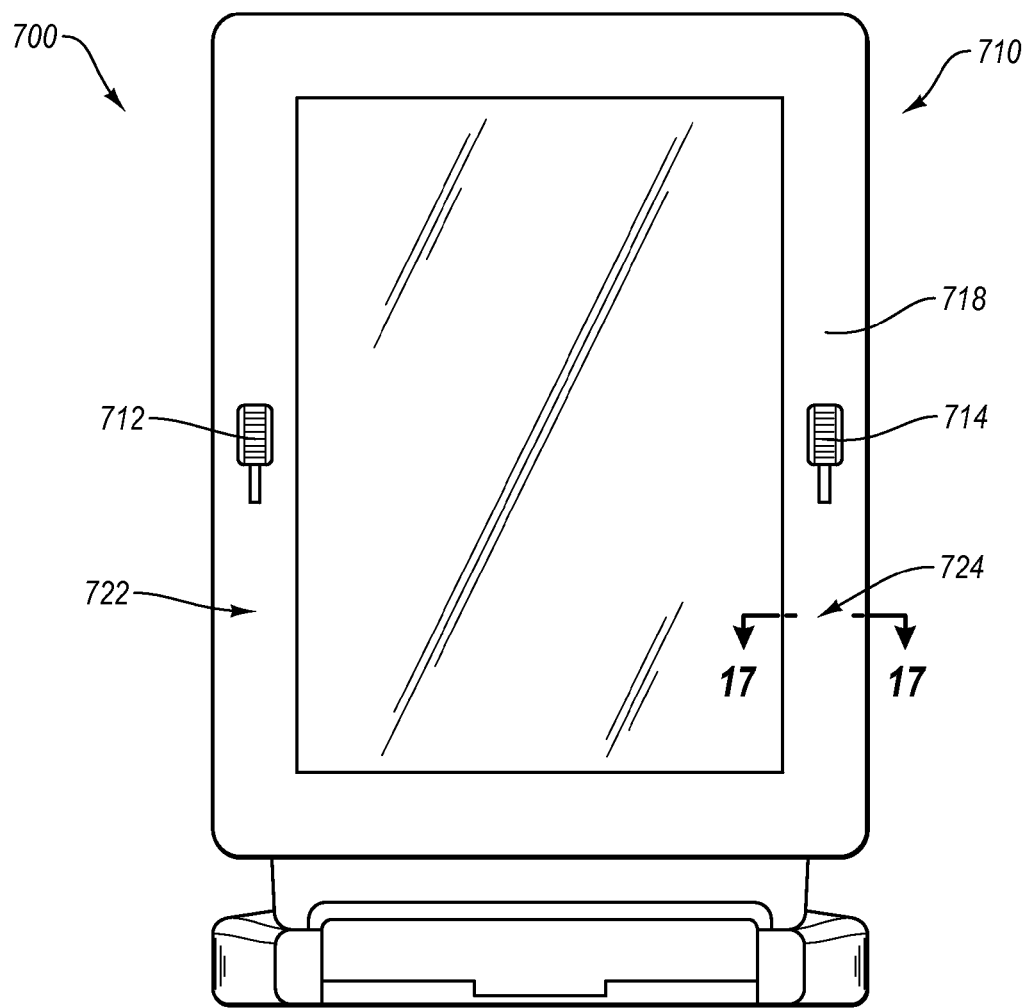
FIG. 16 is front elevation view of another embodiment of a patient monitoring system that includes an embodiment of actuators at a front face of an embodiment of a display unit.

FIG. 16 illustrates another embodiment of a patient monitoring system 700, which can resemble the patient monitoring system 100 in many respects, and which can include a display unit 710 that resembles the display units 110, 610. The display unit 710 can comprise a left actuator 712 and a right actuator 714, which can be incorporated into a front face 718 of the display unit 710. In the illustrated embodiment, the actuators 712, 714 can be displaced downwardly for actuation.

In some embodiments, the actuators 712, 714, which move in a substantially linear path, can be mechanically coupled to a rotational system resembling that discussed above with respect to FIG. 9. For example, the rotational system can include the actuators 122, 124, but with the handles 152, 154 removed. In other embodiments, downward translation of the actuators 712, 714 directly displaces the plungers 322, 324 downwardly.

Figure 17:
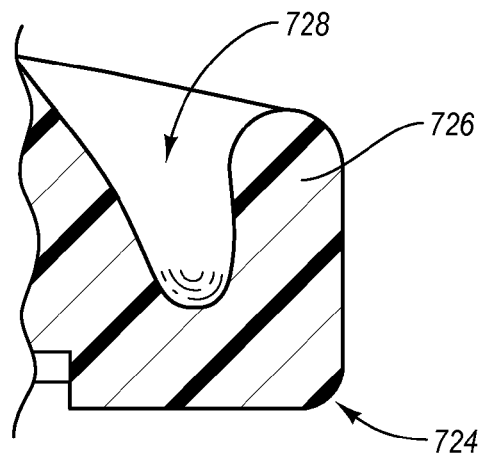
FIG. 17 is a cross-sectional view taken along the view line 17-17 in FIG. 16 illustrating a portion of an embodiment of a gripping region.

The display unit 710 can include a left gripping region 722 and a right gripping region 724. A cross-sectional view of the right gripping region 724 is provided in FIG. 17. The right gripping region 724 can include a finger grip, handlebar, or handle 726, which can be elongated so as to contact one or more fingers. The right gripping region 724 can include a recess 728 sized and shaped to receive one or more fingers. A medical practitioner can grip the right gripping region 724 by clenching the handle 726 with one or more fingers of the right hand 118, and can actuate the right actuator 714 by pulling downwardly with the thumb of the right hand 118.

Figure 18:
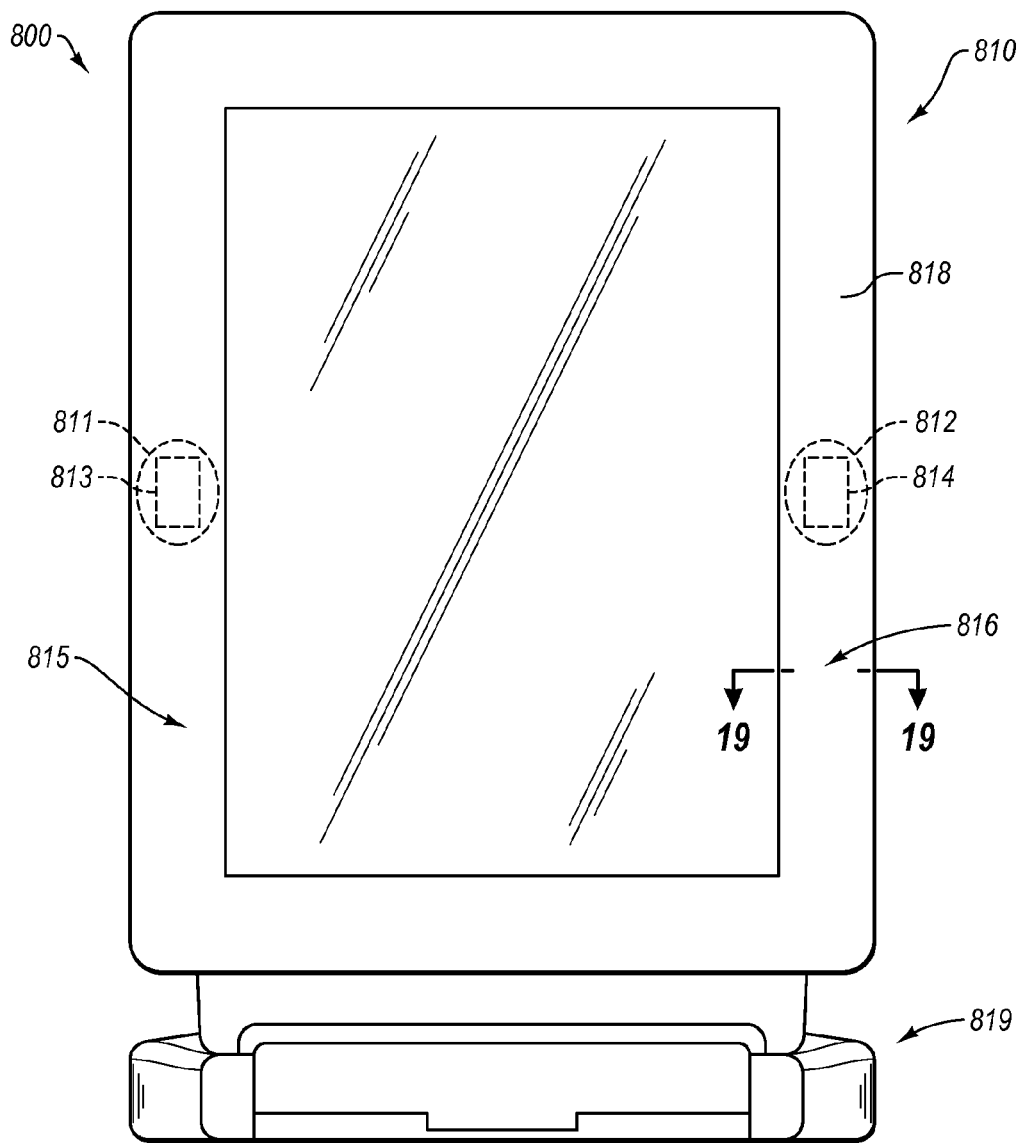
FIG. 18 is a front elevation view of another embodiment of a patient monitoring system that includes another embodiment of actuators at a front face of an embodiment of a display unit.

FIG. 18 illustrates another embodiment of a patient monitoring system 800, which can resemble the patient monitoring systems 100, 700 in many respects, and which can include a display unit 810 that resembles the display units 110, 610, 710. The display unit 810 can comprise a left actuator 811 and a right actuator 812, which can be incorporated into or integral with a front face 818 of the display unit 810. In the illustrated embodiment, the actuators 811, 812 can comprise sensors 813, 814 that are configured to sense a touch, movement, or proximity of the thumb of a medical practitioner's hand 117, 118. For example, in various embodiments, one or more of the sensors 813, 814 can comprise a touch switch, a capacitive sensor, a piezoelectric sensor, a pressure sensor, an infrared sensor, an optical sensor, a light-level sensor, or any other suitable sensor or detector.

The sensors 813, 814 can be configured to communicate electrical signals that actuate release of the display unit 810 from a docking station 819. For example, electrical signals can be delivered to an electric motor that in turn actuates a mechanical system (such as a latch 274, 540) to effect release of the display unit 810 (see, e.g., FIG. 21). As another example, electrical signals can be delivered to an electrical, electromagnetic, or other suitable system to effect release of the display unit 810. For example, the display unit 810 can be coupled with the docking station 819 via an electromagnet, and actuation of the sensors 813, 814 can deactivate the electromagnet.

In some embodiments, the display unit 810 includes only a single actuator 811, 812, which can be used to actuate release of the display unit 810 from the docking station 819. In other embodiments, one or both of the actuators 811, 812 can be actuated in order to permit release of the display unit 810. For example, in some embodiments, actuation of either actuator 811, 812 can be sufficient to permit removal of the display unit 810 from the docking station 819. In other embodiments, both actuators 811, 812 must be actuated in order to permit removal of the display unit 810. In some embodiments, activation of the actuators 811, 812 can be separate, serial, or sequential such that one actuator 811, 812 may be actuated before the other actuator 811, 812. In other embodiments, activation of the actuators 811, 812 must be simultaneous in order to permit or effect removal of the display unit 810. Such an arrangement may, in some instances, advantageously increase the likelihood that a user is gripping two sides of the display unit 810 before the display unit 810 is able to release from the docking station 819.

Figure 19A:
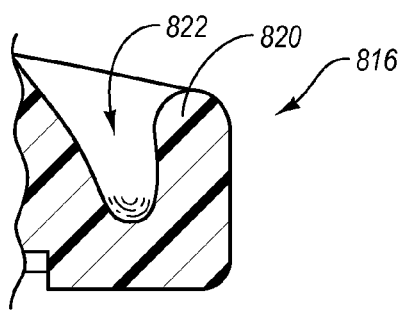
FIG. 19A is a cross-sectional view taken along the view line 19-19 in FIG. 18 illustrating a portion of another embodiment of a gripping region.

The display unit 810 can include a left gripping region 815 and a right gripping region 816 such as the gripping regions 722, 724 discussed above. A cross-sectional view of the right gripping region 816 is provided in FIG. 19A. The right gripping region 816 can include a handle 820 such as the handle 726 discussed above, and can include a recess 822 such as the recess 728 discussed above.

Figure 19B:
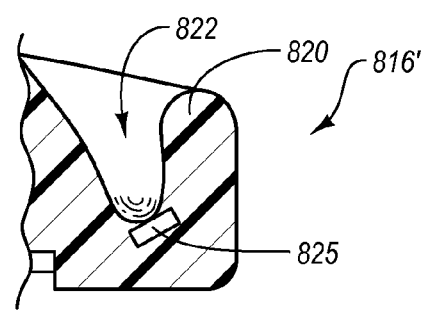
FIG. 19B is a cross-sectional view taken along the view line 19-19 in FIG. 18 illustrating a portion of another embodiment of a gripping region.

FIG. 19B illustrates another embodiment of a right gripping region 816' such as the gripping region 816. The gripping region 816' includes a sensor 825, which can comprise any suitable sensor discussed above. The sensor 825 can be configured to sense the touch, movement, or proximity of one or more fingers of a medical practitioner. The illustrated embodiment includes both the sensor 814 (FIG. 18) and the sensor 825. Activation of both sensors 814, 825, which may be simultaneous, can ensure that a medical practitioner has a firm grasp on the gripping region 816. A similar arrangement of sensors 813, 815 may be used at the left side of the display unit 810. In other embodiments, the display unit 810 comprises a sensor 825 within one or more recesses 822 at either side of the display unit 810 without additional sensors 813, 814 at the front face 818 of the display unit 810.

Figure 20A:
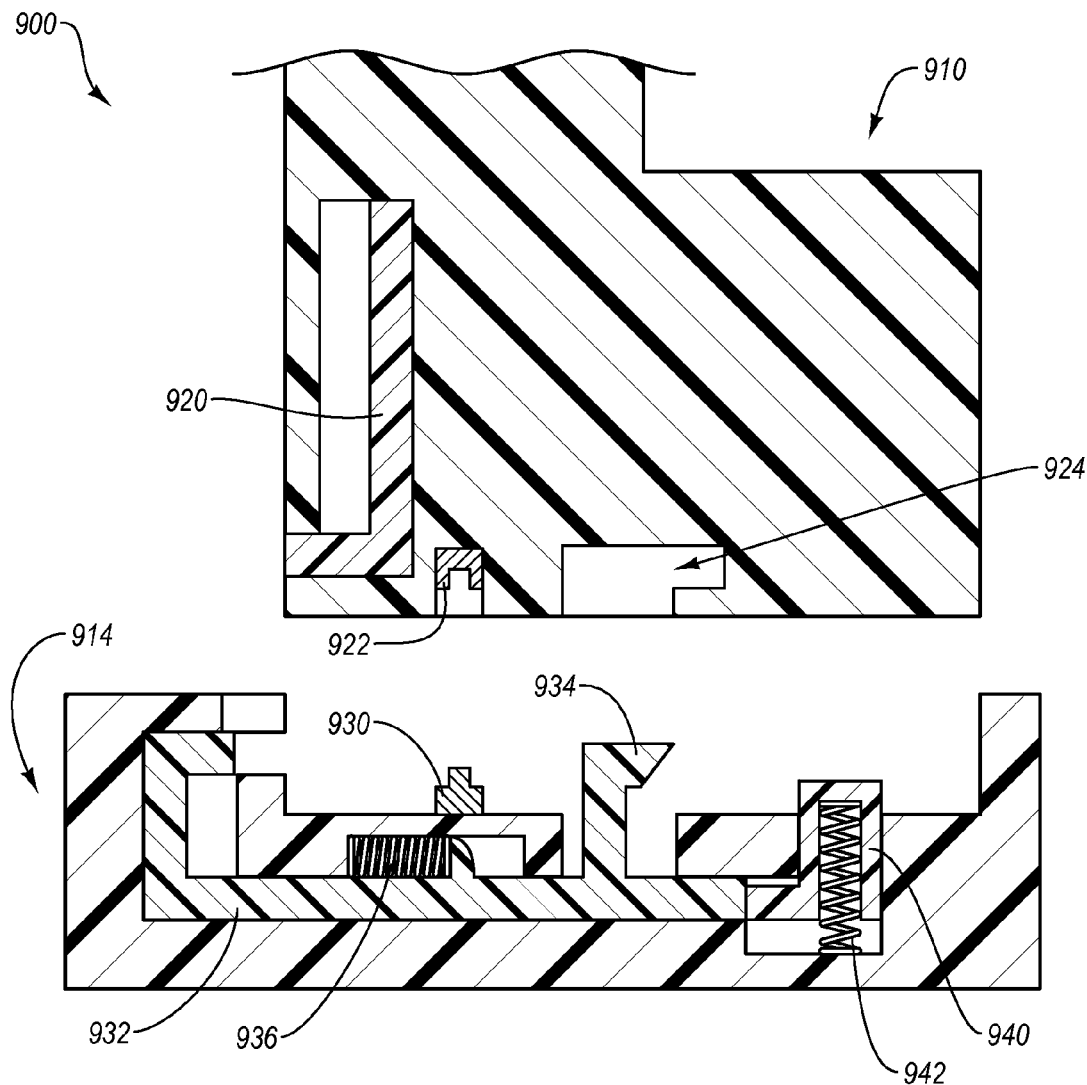
FIG. 20A is a cross-sectional view of another embodiment of a patient monitoring system shown in a disengaged orientation.
Figure 20B:
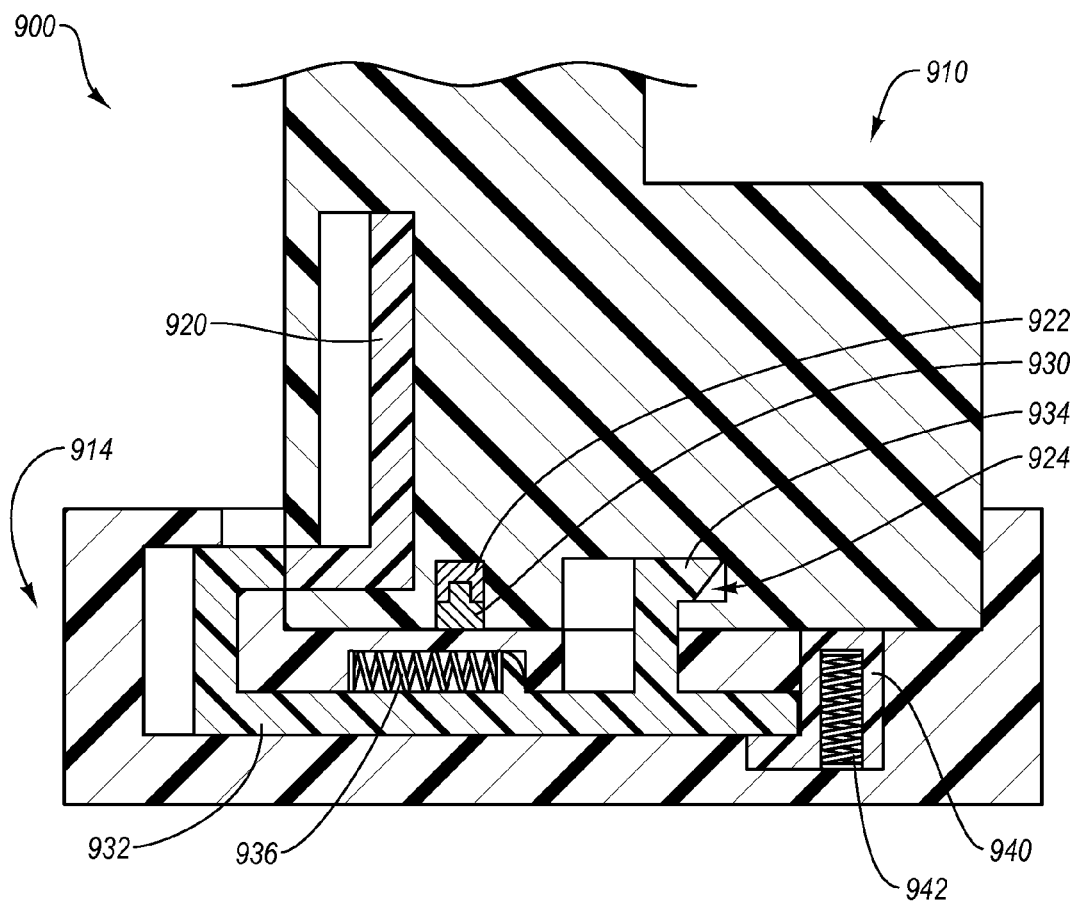
FIG. 20B is a cross-sectional view of the patient monitoring system of FIG. 20A shown in an engaged orientation.
Figure 20C:
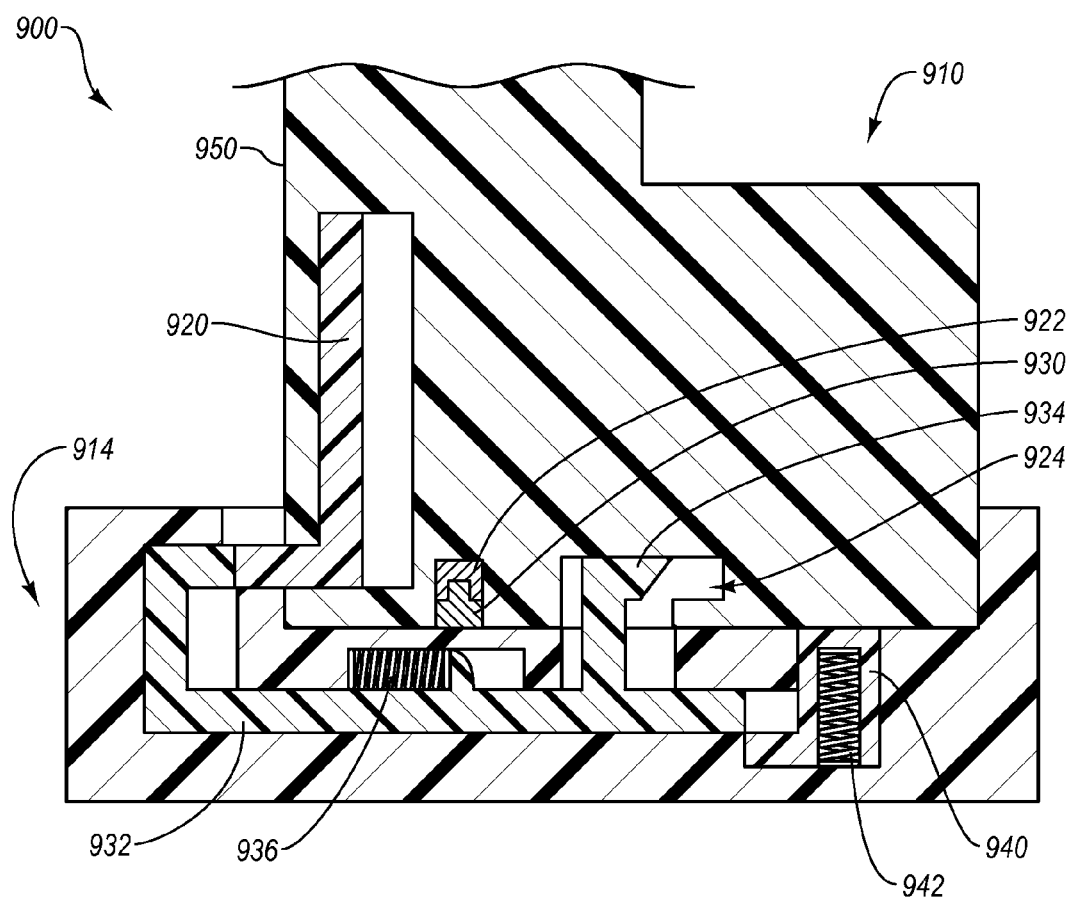
FIG. 20C is a cross-sectional view of the patient monitoring system of FIG. 20A shown in a releasing orientation.

FIGS. 20A-20C illustrate an embodiment of a patient monitoring system 900 that resembles the patient monitoring system 100 in many respects. The system 900 includes a display unit 910 configured to be selectively engaged with and disengaged from a docking station 914. The display unit 910 is configured to be moved downwardly relative to the docking station 914 for engagement and upwardly relative to the docking station 914 for disengagement.

The display unit 910 comprises a right actuator 920, which can be configured to translate in substantially forward and rearward directions relative to the display unit 910. The display unit 910 can comprise a communication port 922, such as the communication port 251 described above. The communication port 922 can be at a bottom end of the display unit 910 in a substantially downward-facing orientation.

The docking station 914 can include a communication port 930, such as the communication port 296 described above. The communication port 930 can be configured to couple with the communication port 922 of the display unit 910, and can be in a substantially upward-facing orientation.

The docking station 914 can include a latch 932 that is configured to translate in substantially forward and rearward directions relative to the docking station 914. The latch 932 can include a catch 934 that is sized and dimensioned to be received in a cavity 924 defined by the display unit 910. The docking station 914 can further comprise a biasing element 936, such as a spring or other suitable device, which biases the latch 932 rearward. The docking station 914 can also include an ejector 940 that is biased upward via a biasing element 942.

FIG. 20A illustrates the system 900 in a disengaged orientation in which the ejector 940 extends upwardly from a lower wall of the docking station 914. In this orientation, the ejector 940 prevents the latch 932 from moving rearward under the bias of the biasing element 936.

FIG. 20B illustrates the system 900 in an engaged orientation in which the communication ports 922, 930 are connected to each other, the ejector 940 is depressed, the biasing element 942 is compressed, the biasing element 936 is extended, and the latch 932 is displaced rearward. To move the system 900 into this orientation, the ejector 940 is displaced downwardly, thereby storing energy in the biasing element 942. The downward displacement of the ejector 940 is sufficient to permit rearward movement of the latch 932 due to the bias of the biasing element 936. This rearward movement introduces the catch 934 into the cavity 924 of the display unit 910, thereby securing the display unit 910 to the docking station 914. The rearward movement also locks the ejector 940 in place against the bias of the biasing element 942.

FIG. 20C illustrates the system 900 in a releasing orientation. To transition the system 900 into this orientation, the right actuator 920 is translated forwardly toward a front face 950 of the display unit 910. The right actuator 920 displaces the plunger forwardly to the same position illustrated in FIG. 20A. In this position, the catch 934 no longer engages the display unit 910, and the ejector 940 is free to move under the bias of the biasing element 942. Accordingly, at an instant after that illustrated in FIG. 20C, the energy stored in the biasing element 942 can be released. In some embodiments, the energy stored in the biasing element 942 is sufficient to move the display unit 910 upward and away from the docking station 914 and disconnect the communication ports 922, 930. In other embodiments, the energy stored in the biasing element 942 is relatively lower, and a user may lift on the display unit 910 in order to separate the communication ports 922, 930 or otherwise separate the display unit 910 from the docking station 914. The amount of lifting force exerted by the user in such instances may be less than would otherwise be required if there were no ejector 940. For certain of such other embodiments, it may be easier to initially couple the display unit 910 with the docking station 914, as compared with certain embodiments where the communication ports 922, 930 are not in an opposing upward/downward facing orientation, as a weight of the display unit 910 may provide sufficient force to couple the communication ports 922, 930 and/or preload the biasing element 942.

Other embodiments of the system 900 can include a left actuator and an additional latch, which can operate in a manner similar to the right actuator 920 and latch 932.

Figure 21:
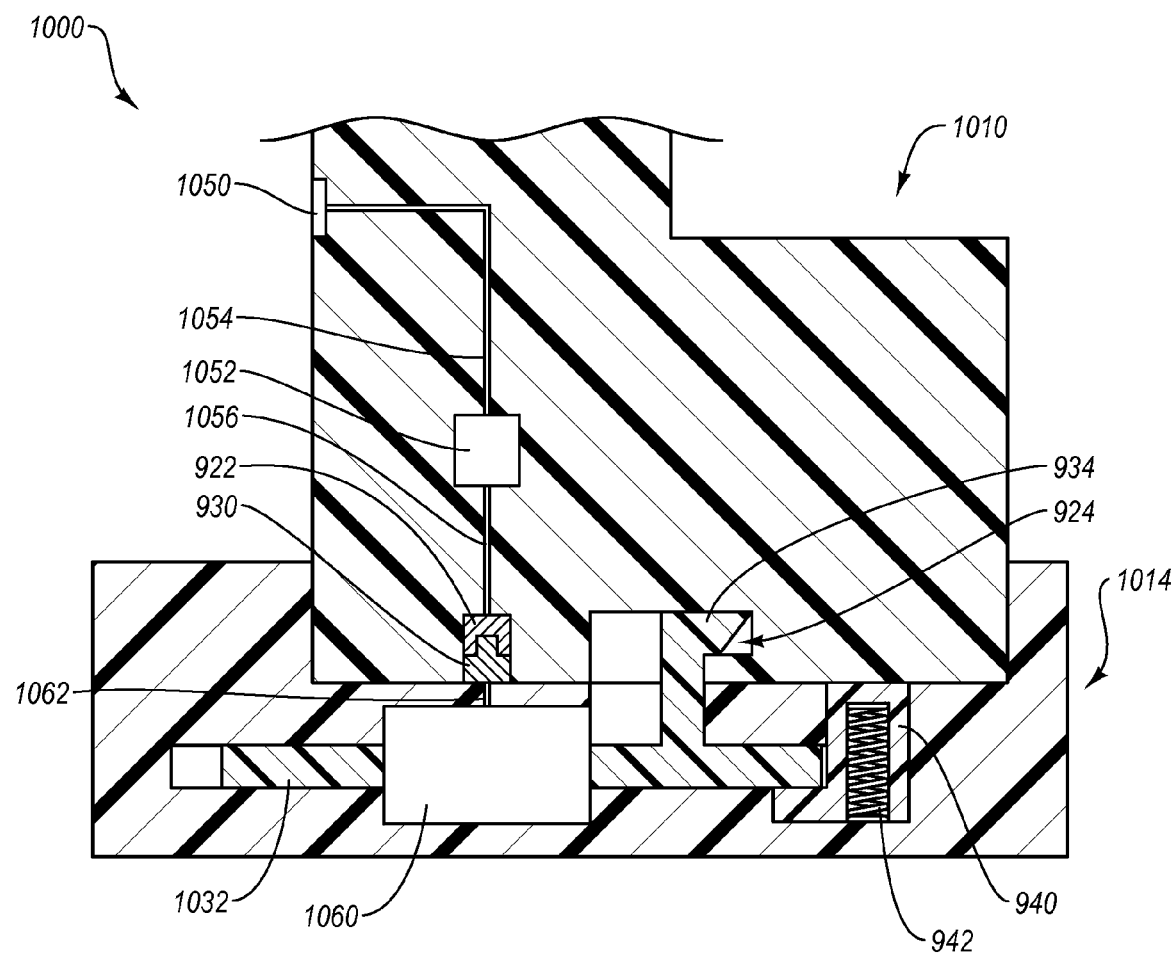
FIG. 21 is a cross-sectional view of another embodiment of a patient monitoring system that includes an electrical motor.

FIG. 21 illustrates an embodiment of a patient monitoring system 1000 that resembles the patient monitoring system 900 in many respects, thus like features are identified with like reference numerals. The system 1000 can include a display unit 1010 and a docking station 1014. The display unit 1010 can include an actuator 1050 and a controller 1052 that can communicate with one another via a communication line 1054. The actuator 1050 can resemble the actuators 811, 812 discussed above, and can include any suitable sensor, such as the sensors 813, 814. The controller 1052 can also be configured to communicate with a communication port 922 via a communication line 1056.

The docking station 1014 can include an electric motor 1060, which can be coupled with a communication port 930 via a communication line 1062. The docking station 1014 can further include a latch 1032, such as the latch 932, which the motor 1060 can move in a forward or rearward direction.

In certain embodiments, as the communication ports 922, 930 are coupled with each other, the motor 1060 can be prompted to move the latch 1032 rearward to insert a catch 934 in a cavity 924 of the display unit 1010 to thereby lock the display unit 1010 in place. The motor 1060 can thus aid in coupling the display unit 1010 to the docking station 1014. Any other suitable locking mechanism may be used.

The motor 1060 can contribute to disengagement of the display unit 1010. Upon actuation of the actuator 1050, a signal can be sent to the controller 1052, which can send a command to the motor 1060 via the communication ports 922, 930 to move the latch 1032 forwardly. Forward movement of the latch 1032 permits an ejector 940 to move under the influence of a biasing element 942 so as to push the display unit 1010 away from the docking station 1014. Other suitable power-assisted mechanisms can be used to aid in coupling and/or decoupling the display unit 1010 and the docking station 1014. For example, in some embodiments, the locking system that includes a latch 1032 is replaced with an electromagnetic system. The display unit 1010 can include a permanent magnet or an electromagnet in a bottom end thereof, and the docking station 1014 can include a permanent magnet or electromagnet in a region that is complementary thereto. Activation of the actuator 1050 can deactivate or reverse the polarity of one or more electromagnets so as to permit or encourage separation of the display unit 1010 from the docking station 1014. In other or further embodiments, the controller 1052 can be located in the docking station 1014.

Although a single actuator 1050 is shown in FIG. 21, in other embodiments, the display unit 1010 can include two or more actuators, such as the actuators 811, 812 discussed above. The multiple actuators may operate in manners such as those described with respect to the actuators 811, 812. For example, in some embodiments, the actuators 811, 812 may be activated serially in order to permit removal of the display unit 1010, whereas in other embodiments, the actuators 811, 812 must be activated simultaneously. As used herein, the term "simultaneously" includes situations in which both actuators 811, 812 are activated at the same time, as well as situations in which one of the actuators 811, 812 is initially activated before the other actuator 811, 812 and is maintained in an activated state while the second actuator 811, 812 is eventually activated.

Power-assisted release mechanisms, such as those described with respect to the patient monitoring system 1000, can be employed in systems where the communication ports 922, 930 attach to each other in other manners, such as any of the forward/rearward facing arrangements described above. For example, in some embodiments, a motor may be used to displace a latch (e.g., the latch 242) or latch members (e.g., the latch members 542, 544) downwardly when the actuators 813, 814 of the display unit 810 are activated (see FIG. 18).

Figure 22:
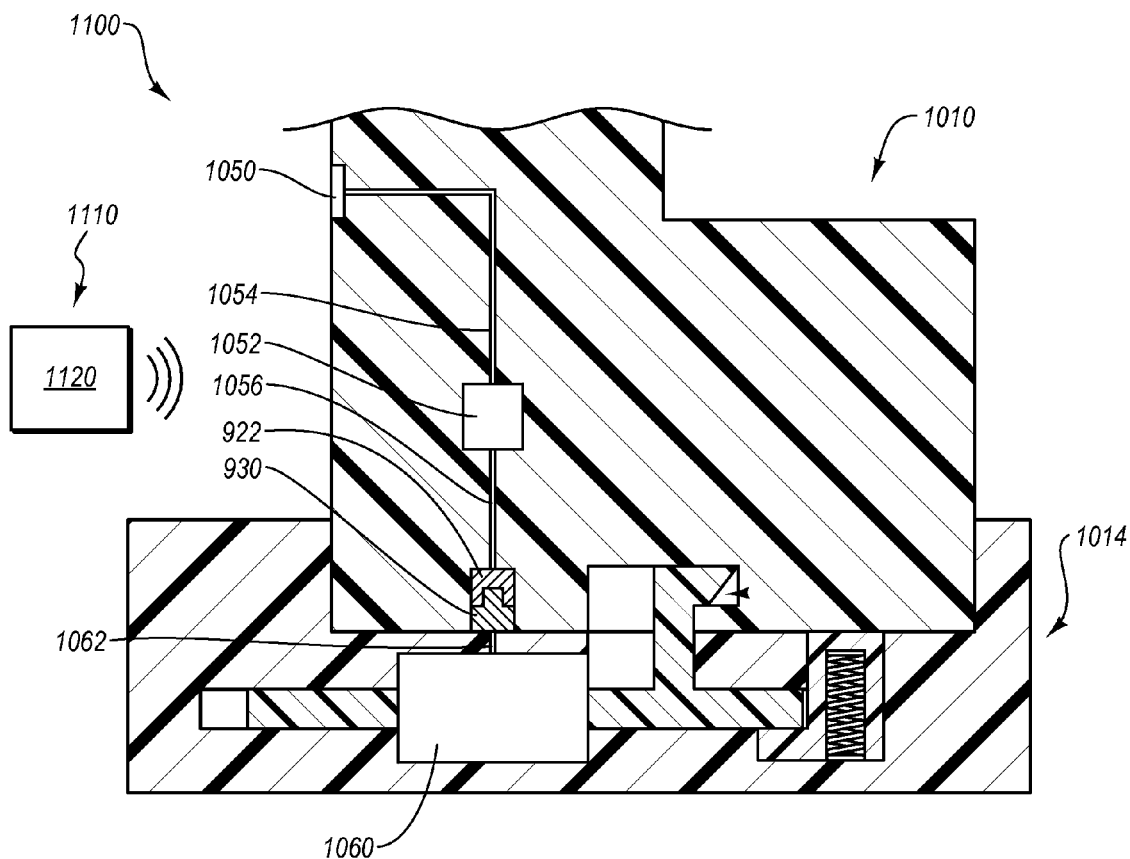
FIG. 22 is a cross-sectional view of another embodiment of a patient monitoring system that is configured to permit decoupling of a display unit from a docking station based on information received from an identification device.

FIG. 22 illustrates an embodiment of a patient monitoring system 1100 that resembles the patient monitoring systems 900, 1000 in many respects, thus like features are identified with like reference numerals. The system 1100 can include a display unit 1010, which includes one or more actuators 1050 and a controller 1052, and also can include a docking station 1014. The system 1100 can further include communication lines 1054, 1056, 1062 and a motor 1060.

The system 1100 can further include a communicator 1110 that is configured to provide authorization information to the controller 1052, whether directly or indirectly. For example, the communicator 1110 can be configured to communicate with the controller 1052 directly via a wireless protocol, or the communicator 1110 can be configured to communicate directly with the actuator 1050 via a wireless protocol, and the actuator 1050 can then deliver information received from the communicator 1110 to the controller 1052.

Information provided by the communicator 1110 can indicate that the possessor of the communicator 1110 is authorized to remove the display unit 1010 from the docking station 1014. The controller 1052 may be programmed or otherwise configured to allow proper operation of the one or more actuators 1050 only after authorization information is received. In other or further embodiments, the controller 1052 may be programmed to allow proper operation of the one or more actuators 1050 only within a time frame that is concurrent with the receipt of such authorization information. For example, the communicator 1110 may continuously, or substantially continuously, transmit authorization information to the controller 1052 only when the controller 1052 is within range of the communicator 1110. By way of illustration, the controller 1052 may only receive authorization information from the communicator 1110 when the communicator 1110 is within the same room as the controller 1052 and/or is within several meters of the controller 1052. As another example, the communicator 1110 may provide information to the controller 1052 that includes information regarding the location of the communicator 1110, and the controller 1052 may only permit operation of the one or more actuators 1050 when the location information indicates that the communicator 1110 is within a specified region. As previously discussed, the controller 1052 may be comprised in one or more of the display unit 1010 and the docking station 1014.

In the illustrated embodiment, the communicator 1110 comprises a radio-frequency identification (RFID) tag (e.g., a passive RFID tag) 1120, which may, for example, be situated on a bracelet, employee tag, or the like, that identifies the wearer or possessor thereof as a hospital employee. Upon receiving authorization information from the RFID tag 1120, the controller 1052 can enter an "authorized" mode in which activation of the actuators 1050 can cause the controller to activate the motor 1060 in manners such as described above. On the other hand, if no such authorization information is received by the controller 1052, the controller 1052 may operate in an "unauthorized" mode and would not activate the motor 1060 upon actuation of the actuators 1050.

The system 1100 thus can prevent the unauthorized removal of a display unit 1010 from the docking station 1014. Thus, in some situations, hospital employees may be able to undock the display unit 1010, whereas visitors or patients cannot. In further situations, only hospital employees with a given authorization level may permitted to undock the display unit 1010, whereas other employees cannot. Any other suitable authorization system and/or communication protocol may be used. For example, in various embodiments, the communicator 1110 can comprise any suitable transmitter or transceiver, and the controller 1052 can comprise any suitable receiver or transceiver that is configured to communicate with the communicator 1110 via any suitable wireless system or protocol, such as, for example, radiofrequency (e.g., Bluetooth™, ZigBee), infrared, magnetic inductance, etc. In still other embodiments, the communication may be established in a wired or tethered fashion. In still other embodiments, a magnetic card reader or a physical keying system may be used.

Figure 23:
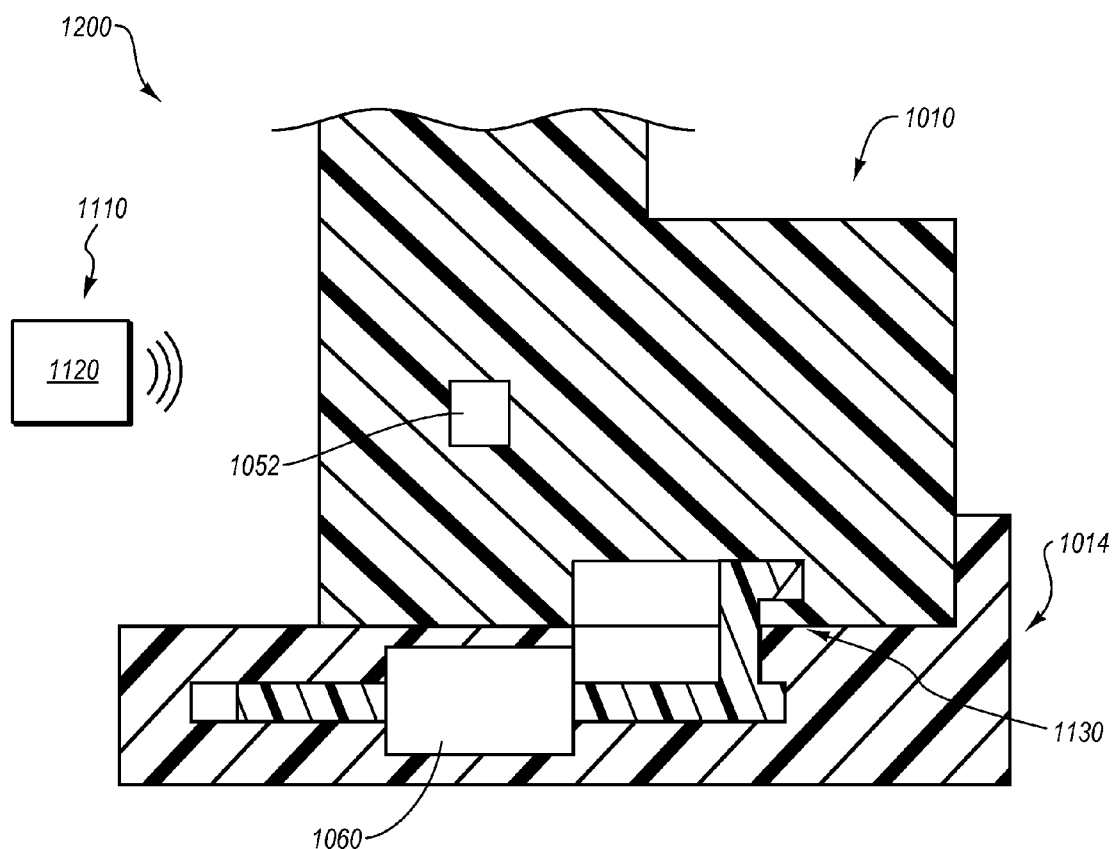
FIG. 23 is a cross-sectional view of another embodiment of a patient monitoring system that is configured to permit decoupling of a display unit from a docking station based on information received from an identification device.

FIG. 23 schematically illustrates an embodiment of a patient monitoring system 1200 that resembles the patient monitoring systems 100, 900, 1000, 1100 in many respects, thus like features are identified with like reference numerals. The system 1200 can include a display unit 1010 and a docking station 1014 that closely resemble the display unit 110 and the docking station 114 described above. For example, the display unit 1010 can include actuators 122, 124 that are configured to cooperate with a latch 242 in a manner such as described above with respect to the display unit 110 and the docking station 114.

The system 1200 can further include an automated lock 1130, which can include a motor 1060, as well as a controller 1052 that is configured to operate the motor 1060. A communicator 1110, such as an RFID tag 1120, can be configured to communicate with the controller 1052 in manners such as described above.

In use, the lock 1130 can operate automatically. For example, the controller 1052 can automatically move the lock 1130 into an unlocked orientation when it receives authentication information from the communicator 1110. Communication between the controller 1052 and the motor 1060 may be wireless or wired. For example, communication leads 1054, 1056, 1062 (not shown in FIG. 23) may be used in conjunction with forward/rearward facing communication ports (such as the communication ports 251, 296 in FIGS. 4 and 5). In certain embodiments, when the controller 1052 is out of range, the controller 1052 can move the lock 1130 into a locked configuration.

Further embodiments of the systems and devices disclosed herein are also possible. In some embodiments, one or more components or features of the systems are reversed. For example, in some embodiments, one or more alignment posts 260 are positioned on a docking station, such as the docking station 114, and one or more corresponding channels 290 are positioned within the docking cavity 250 of a display unit, such as the display unit 110. The channels 290 can be substantially upside-down relative to the orientation shown in FIG. 5.

In some embodiments, a display unit comprises a movable latch, such as, for example, one of the latches 274, 540, 932, 1032 described above. Actuators can be used to move the latch, which can allow separation from a docking station. The latch can be configured to rotate and/or translate, and may move in a sideways, upward, downward, forward, and/or rearward direction.

In some embodiments, a display unit comprises gripping regions at its sides that substantially resemble the upper gripping region 615 (FIG. 15). The gripping regions can be oriented sideways relative to the configuration shown in FIG. 15. For example, as a medical practitioner grasps the side gripping regions, the practitioner's fingers can extend through an opening defined between a gripping region and a viewing area of the display unit, and can point back toward the practitioner (e.g., in a forward direction).

Much of the foregoing discussion made with respect to a single set of features, where two sets of such features are disclosed, can apply equally to the other set of features not specifically discussed. Thus, as an example, descriptions relative to one of the left or right portions of the display unit 110 can, in some embodiments, apply as appropriate to the other of the left and right portions of the display unit 110.

The foregoing disclosure recites various embodiments that include gripping features and actuation features. Examples of means for gripping a display unit include the gripping regions 115, 116, 615, 722, 724, 815, 816, and 816'. Examples of means for actuating release of a display unit from a docking station include the actuators 122, 124, 612, 712, 714, 811, 812, 825, 920, and 1050.

Methods related to the disclosed patient monitoring systems, such as the systems 100, 700, 800, 900, 1000, 1100, and 1200, their respective components and features, and their use are supported by this disclosure and will be evident to the skilled practitioner. For example, actions described in this disclosure can form the basis of method steps. Moreover, any suitable combination of actions disclosed with respect to the patient monitoring systems, and their respective components and features, is contemplated by this disclosure.

Additionally, any suitable combination of the disclosed patient monitoring systems, such as the systems 100, 700, 800, 900, 1000, 1100, and 1200 and their respective components and features, is contemplated by this disclosure. By way of example, any of the display units 610, 710, 810 can be used with either of the docking stations 114, 514.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 ¶6.

What is claimed is:

1. A display system comprising:
   a docking station configured to be mounted in a substantially fixed position;
   a display unit configured to display information, the display unit configured to be selectively coupled with the docking station and to be selectively decoupled from the docking station, wherein the display unit comprises a first gripping region configured to be grasped by a hand so as to bear at least a portion of the weight of the display unit when the display unit is separated from the docking station; and
   a first actuator configured to aid in decoupling the display unit from the docking station when actuated, wherein the first actuator is positioned so as to be actuated by the same hand that grasps the first gripping region of the display unit while the first gripping region is being grasped.

2. The system according to claim 1, wherein the display unit comprises the first actuator.

3. The system according to claim 2, wherein the first actuator is movable relative to the docking station such that actuation of the first actuator mechanically transfers force to effectuate separation of the display unit from the docking station.

4. The system according to claim 1, wherein the display unit comprises an upper end and a lower end, wherein the upper end is configured to be oriented upwardly when the display unit is coupled with the docking station, and wherein at least a portion of the first gripping region is closer to the lower end than it is to the upper end.

5. The system according to claim 4, wherein the display unit comprises the first actuator, and wherein the first actuator is closer to the lower end of the display unit than it is to the upper end of the display unit.

6. The system according to claim 1, wherein the display unit comprises a center of gravity, and wherein the center of gravity and at least a portion of the first gripping region are higher than a bottom face of the display unit by the same amount when the display unit is coupled with the docking station.

7. The system according to claim 1, wherein the first gripping region of the display unit comprises at least a portion of the first actuator.

8. The system according to claim 1, wherein the first actuator is configured to be actuated by tightening the grasp of the hand on the first gripping region.

9. The system according to claim 1, wherein the first actuator is configured to be rotated relative to the docking station to permit separation of the display unit from the docking station.

10. The system according to claim 1, wherein the first actuator is integral with a front face of the display unit.

11. The system according to claim 1, wherein the first gripping region is configured to be grasped by one or more fingers of a hand and the first actuator is configured to be actuated by the thumb of the hand while the one or more fingers grasp the first gripping region.

12. The system according to claim 1, wherein the first actuator comprises a sensor configured to sense a proximity or a movement of at least a portion of a hand.

13. The system according to claim 12, wherein the first actuator comprises one or more of a touch switch, a capacitive sensor, a piezoelectric sensor, a pressure sensor, an infrared sensor, an optical sensor, and a light-level sensor.

14. The system according to claim 1, wherein the first actuator is configured to activate an electric motor to assist in decoupling the display unit from the docking station.

15. The system according to claim 1, wherein the docking station comprises a first electrical connector and the display unit comprises a second electrical connector, and wherein the first and second electrical connectors are configured to couple with each other as the display unit is coupled with the docking station.

16. The system according to claim 15, wherein one of the first and second electrical connectors is configured to be substantially forward-facing and the other of the first and second electrical connectors is configured to be substantially rearward-facing when the docking station is mounted in a substantially fixed position and is coupled with the display unit.

17. The system according to claim 15, wherein one of the first and second electrical connectors is configured to be substantially upward-facing and the other of the first and second electrical connectors is configured to be substantially downward-facing when the docking station is mounted in a substantially fixed position and is coupled with the display unit.

18. The system according to claim 1, wherein one of the docking station and the display unit comprises a latch, and wherein actuation of the first actuator effects movement of the latch.

19. The system according to claim 18, wherein the first actuator is configured to be moved into at least a first and a second orientation during actuation, wherein the first actuator displaces the latch so as to permit decoupling of the display unit from the docking station when moved into the first orientation, and wherein the first actuator urges the display unit to separate from the docking station when moved into the second orientation.

20. The system according to claim 18, further comprising a lip configured to move from a first position when the latch is in an unlocked orientation to a second position when the latch is in a locked orientation to thereby provide a visually perceivable indication regarding whether the latch is in the locked orientation.

21. The system according to claim 1, wherein one of the docking station and the display unit comprises a groove and the other of the docking station and the display unit comprises a protrusion configured to be received within the groove so as to aid in coupling the docking station to the display unit, and wherein at least a portion of the groove is configured to direct the display unit downwardly relative to the docking station during the coupling.

22. The system according to claim 1, wherein the docking station comprises a projection configured to be gripped so as to aid in coupling the display unit with the docking station.

23. The system according to claim 1, further comprising a communicator and a controller, wherein the controller is configured to allow removal of the display unit from the docking station only after the controller receives authorization information from the communicator.

24. The system according to claim 23, wherein the communicator comprises an RFID tag.

25. The system according to claim 1, further comprising:
a second gripping region configured to be grasped by a hand so as to bear at least a portion of the weight of the display unit when the display unit is separated from the docking station; and
a second actuator configured to aid in decoupling the display unit from the docking station when actuated, wherein the second actuator is positioned so as to be actuated by the same hand that grasps the second gripping region of the display unit while the second gripping region is being grasped.

26. The system according to claim 25, wherein the first and second gripping regions are at opposite sides of the display unit.

27. The system according to claim 25, wherein the first gripping region is at a side of the display unit and the second gripping region is at an upper end of the display unit.

28. The system according to claim 25, wherein actuation of one or more of the first and second actuators effects decoupling of the display unit from the docking station.

29. The system according to claim 25, wherein actuation of each of the first and second actuators is required in order to decouple the display unit from the docking station.

30. The system according to claim 29, wherein each of the first and second actuators comprise a sensor configured to sense a proximity or a movement of at least a portion of a hand.

31. The system according to claim 30, wherein actuation of the first and second actuators is configured to activate an electric motor to assist in decoupling the display unit from the docking station.

32. The system according to claim 29, wherein actuation of the first actuator can occur at a different time than actuation of the second actuator to permit decoupling of the display unit from the docking station.

33. A display unit for use in monitoring a patient, the display unit configured to selectively couple with and decouple from a docking station mounted in a hospital room, the display unit comprising:
a first gripping region configured to be grasped by a hand of a medical practitioner so as to bear at least a portion of the weight of the display unit; and
a first actuator, wherein the first actuator is configured to aid in decoupling the display unit from the docking station, and wherein the first actuator is positioned so as to be actuated by the same hand that grasps the first gripping region while the first gripping region is being grasped.

34. The display unit according to claim 33, further comprising a viewing area configured to display information in a predefined orientation such that the viewing area comprises an upper end and a lower end, and such that the display unit correspondingly comprises an upper end and a lower end, wherein the first gripping region is closer to the lower end of the display unit than it is to the upper end of the display unit.

35. The display unit according to claim 33, further comprising:
a second gripping region configured to be grasped by a hand of a medical practitioner so as to bear at least a portion of the weight of the display unit; and
a second actuator, wherein the second actuator is configured to aid in decoupling the display unit from the docking station, and wherein the second actuator is positioned so as to be actuated by the same hand that grasps the second gripping region while the second gripping region is being grasped.

36. The display unit according to claim 35, wherein the first and second gripping regions are at different sides of the display unit.

37. The display unit according to claim 36, wherein the first and second gripping regions are at opposite sides of the display unit.

38. A display unit for use in monitoring a patient, the display unit configured to selectively couple with and decouple from a docking station mounted in a hospital room, the display unit comprising:
a screen configured to display information in a predetermined orientation such that the screen comprises an upper end and a lower end, and such that the display unit correspondingly comprises an upper end and a lower end;

a gripping region configured to be grasped by a hand of a medical practitioner, the gripping region being closer to the lower end of the display unit than to the upper end of the display unit; and an actuator configured to aid in decoupling the display unit from the docking station, wherein at least a portion of the actuator is within the gripping region.

39. The display unit according to claim 38, wherein the display unit comprises a center of gravity that is closer to the lower end of the display unit than to the upper end of the display unit.

40. The display unit according to claim 38, wherein the actuator comprises an elongated finger grip.

41. The display unit according to claim 40, wherein the finger grip is elongated in a direction substantially parallel to a side edge of the screen that extends between the upper and the lower end.

42. A display unit for use in monitoring a patient, the display unit configured to selectively couple with and decouple from a docking station mounted in a hospital room, the display unit comprising:

a front face that comprises a viewing area configured to display information in a predetermined orientation such that the viewing area comprises an upper end and a lower end, and such that the display unit correspondingly comprises an upper end and a lower end, wherein the display unit further comprises a rearward end;

a center of gravity at a position rearward of the front face, forward of the rearward end, higher than the lower end, and lower than the upper end when the display unit is in an upright orientation;

a first gripping region in a first side of the display unit, wherein the center of gravity and a portion of the first gripping region are higher than the lower end of the display unit by the same amount when the display unit is in the upright orientation; and a first actuator configured to release the display unit from the docking station.

43. The display unit according to claim 42, wherein the center of gravity and at least a portion of the first gripping region are rearward of the front face by the same amount when the display unit is in the upright orientation.

44. The display unit according to claim 42, wherein the amount by which the center of gravity is higher than the lower end of the display unit is less than the amount by which the center of gravity is lower than the upper end of the display unit.

45. The display unit according to claim 42, wherein the first gripping region is configured to be grasped by a hand of a medical practitioner, and wherein the first actuator is positioned relative to the first gripping region to be within reach of the hand of the medical practitioner during said grasping of the gripping region.

46. The display unit according to claim 42, wherein the first actuator comprises a handle that is within the gripping region.

47. The display unit according to claim 46, wherein the handle is configured to rotate relative to the front face of the display unit.

48. The display unit according to claim 42, wherein the actuator is disposed in the front face of the display unit.

49. The display unit according to claim 42, further comprising a second gripping region in a second side of the display unit and a second actuator configured to release the display unit from the docking station.

50. A display unit for use in monitoring a patient, the display unit configured to selectively couple with and decouple from a docking station mounted in a hospital room, the display unit comprising:

a front surface that comprises a screen, wherein the display unit comprises an upper end, a lower end, and a side face when the display unit is in an upright orientation that corresponds with an upright orientation of the screen;

a gripping region that comprises a portion of the front face and a portion of the side face, wherein the gripping region is configured to receive a hand of a medical professional such that a first portion of the hand contacts the front face and a second portion of the hand contacts the side face when the hand grasps the gripping region so as to bear at least a portion of the weight of the display unit; and an actuator configured to release the display unit from the docking station.

51. The display unit according to claim 50, wherein at least a portion of the actuator is within the gripping region.

52. The display unit according to claim 50, wherein the actuator is positioned relative to the gripping region so as to be within reach of a hand of a medical practitioner that grasps of the gripping region.

53. A system for monitoring a patient, the system comprising:

a docking station configured to be mounted in a substantially fixed position;

a display unit configured to display information regarding a patient, the display unit configured to be selectively coupled with the docking station and to be selectively decoupled from the docking station, wherein the display unit comprises means for gripping the display unit; and means for actuating release of the display unit from the docking station, wherein, when the display unit and the docking station are coupled with each other, the means for actuating release of the display unit is configured to be actuated by a hand of a medical practitioner while the means for gripping the display unit is being grasped by the hand.

54. The system according to claim 53, wherein the means for gripping the display unit comprises at least a portion of the means for actuating release of the display unit.

55. The system according to claim 53, further comprising an additional means for gripping the display unit and an additional means for actuating release of the display unit, wherein, when the display unit and the docking station are coupled with each other, the additional means for actuating release of the display unit is configured to be actuated by an additional hand of the medical practitioner while the additional means for gripping the display unit is being grasped by the additional hand.

* * * * *